(12) United States Patent
Cavalcanti et al.

(10) Patent No.: US 7,749,184 B2
(45) Date of Patent: Jul. 6, 2010

(54) APPARATUS AND METHOD OF MONITORING A VASCULAR ACCESS OF A PATIENT SUBJECTED TO AN EXTRACORPOREAL BLOOD TREATMENT

(75) Inventors: Silvio Cavalcanti, Bologna (IT); Carlo Alberto Lodi, Carpi (IT); Massimo Fava, Mirandola (IT)

(73) Assignee: Gambro Lundia AB (SE)

( * ) Notice: Subject to any disclaimer, the term of this patent is extended or adjusted under 35 U.S.C. 154(b) by 675 days.

(21) Appl. No.: 11/641,874

(22) Filed: Dec. 20, 2006

(65) Prior Publication Data

US 2007/0112289 A1 May 17, 2007

Related U.S. Application Data

(62) Division of application No. 10/765,149, filed on Jan. 28, 2004, now Pat. No. 7,172,570.

(60) Provisional application No. 60/466,052, filed on Apr. 29, 2003.

(30) Foreign Application Priority Data

Jan. 28, 2003 (IT) .......................... MO2003A0018

(51) Int. Cl.
*A61M 37/00* (2006.01)
*A61M 1/36* (2006.01)
*C02F 1/44* (2006.01)

(52) U.S. Cl. .................... 604/6.11; 604/4.01; 604/5.01; 604/31; 210/645; 210/739; 210/87

(58) Field of Classification Search ................ 604/4.01, 604/5.01, 6.11, 5.04, 65–67; 210/600, 633, 210/645, 646, 739, 741, 742, 743, 746, 416.1; 422/44

See application file for complete search history.

(56) References Cited

U.S. PATENT DOCUMENTS 2,709,785 A 5/1955 Fielden (Continued)

FOREIGN PATENT DOCUMENTS

DE 4024434 2/1992

(Continued)

OTHER PUBLICATIONS

Hester, et al.; "A new Technique for Determining Recirculation in the ESRD Patient", Nephrology News & Issues, pp. 44-45, (1993).

(Continued)

*Primary Examiner*—Leslie R Deak
(74) *Attorney, Agent, or Firm*—Finnegan, Henderson, Farabow, Garrett & Dunner LLP

(57) ABSTRACT

In the apparatus and method for monitoring a vascular access (6) of an extracorporeal circuit (5; 10) of a patient, a control and calculation unit (17) varies a flow rate of a blood pump (9) predisposed to cause blood to circulate in the extracorporeal circuit. The control and calculation unit receives the pressure values in the blood withdrawal line (5) and the blood return line (10) from two pressure sensors (8, 12); the pressure values are a series of different values of the blood flow rate. The control and calculation unit processes the data gathered by means of a mathematical model which describes the variation of pressure in the vascular access as a function of the flow rate, in order to determine the blood flow rate in the vascular access. The invention detects the presence and location of a stenosis at the vascular access of a patient subjected to a hemodialysis treatment.

42 Claims, 3 Drawing Sheets

U.S. PATENT DOCUMENTS

| | | |
|---|---|---|
| 3,324,720 A | 6/1967 | Sutherland |
| 3,396,331 A | 8/1968 | Sperry, III |
| 3,404,336 A | 10/1968 | Rosenthal |
| 3,433,935 A | 3/1969 | Sherman |
| 3,446,073 A | 5/1969 | Auphan et al. |
| 3,450,984 A | 6/1969 | Holmes |
| 3,482,575 A | 12/1969 | Claff et al. |
| 3,491,592 A | 1/1970 | Evers et al. |
| 3,545,428 A | 12/1970 | Webster, Jr. |
| 3,561,266 A | 2/1971 | Auphan et al. |
| 3,604,263 A | 9/1971 | Auphan et al. |
| 3,619,423 A | 11/1971 | Galletti et al. |
| 3,640,271 A | 2/1972 | Horton |
| 3,722,276 A | 3/1973 | Chandler et al. |
| 3,733,899 A | 5/1973 | Auphan et al. |
| 3,867,688 A | 2/1975 | Koshi |
| 3,946,731 A * | 3/1976 | Lichtenstein .................. 604/66 |
| 3,964,479 A | 6/1976 | Boag et al. |
| 3,980,346 A | 9/1976 | Leiber |
| 3,980,946 A | 9/1976 | Fleury |
| 3,985,134 A | 10/1976 | Lissot et al. |
| 3,987,788 A | 10/1976 | Emil |
| 4,081,372 A | 3/1978 | Atkin et al. |
| 4,136,563 A | 1/1979 | Mueller et al. |
| 4,138,639 A | 2/1979 | Hutchins |
| 4,153,418 A | 5/1979 | Haas |
| 4,167,870 A | 9/1979 | Haas |
| 4,181,610 A | 1/1980 | Shintani et al. |
| 4,361,049 A | 11/1982 | Volgyesi |
| 4,391,124 A | 7/1983 | Drost et al. |
| 4,432,231 A | 2/1984 | Napp et al. |
| 4,434,648 A | 3/1984 | Drost et al. |
| 4,446,871 A | 5/1984 | Imura |
| 4,508,622 A | 4/1985 | Polaschegg et al. |
| 4,650,458 A | 3/1987 | Dahlberg et al. |
| 4,715,849 A | 12/1987 | Gion et al. |
| 4,739,492 A | 4/1988 | Cochran |
| 4,740,755 A | 4/1988 | Ogawa |
| 4,777,938 A | 10/1988 | Sirota |
| 4,797,655 A | 1/1989 | Orndal et al. |
| 4,822,341 A | 4/1989 | Colone |
| 4,825,168 A | 4/1989 | Ogawa et al. |
| 4,856,321 A | 8/1989 | Smalling et al. |
| 4,885,001 A | 12/1989 | Leppert |
| 4,885,087 A | 12/1989 | Kopf |
| 4,923,598 A | 5/1990 | Schäl |
| 4,995,268 A | 2/1991 | Ash et al. |
| 5,004,459 A | 4/1991 | Peabody et al. |
| 5,024,756 A | 6/1991 | Sternby |
| 5,058,416 A | 10/1991 | Engelhardt et al. |
| 5,092,836 A | 3/1992 | Polaschegg |
| 5,098,373 A | 3/1992 | Polaschegg |
| 5,100,554 A | 3/1992 | Polaschegg |
| 5,230,341 A | 7/1993 | Polaschegg |
| 5,312,550 A | 5/1994 | Hester |
| 5,357,967 A | 10/1994 | Dixon et al. |
| 5,372,136 A | 12/1994 | Steuer et al. |
| 5,442,969 A | 8/1995 | Troutner et al. |
| 5,453,576 A | 9/1995 | Krivitski |
| 5,507,723 A | 4/1996 | Keshaviah |
| 5,510,716 A | 4/1996 | Buffaloe, IV et al. |
| 5,510,717 A | 4/1996 | Buffaloe, IV et al. |
| 5,518,623 A | 5/1996 | Keshaviah et al. |
| 5,570,026 A | 10/1996 | Buffaloe, IV et al. |
| 5,588,959 A | 12/1996 | Ahmad et al. |
| 5,595,182 A | 1/1997 | Krivitski |
| 5,605,630 A | 2/1997 | Shibata |
| 5,644,240 A | 7/1997 | Brugger |
| 5,662,806 A | 9/1997 | Keshaviah et al. |
| 5,685,988 A | 11/1997 | Malchesky |
| 5,685,989 A | 11/1997 | Krivitski et al. |
| 5,830,365 A | 11/1998 | Schneditz |
| 5,866,015 A * | 2/1999 | Kramer ...................... 210/739 |
| 5,894,011 A | 4/1999 | Prosl et al. |
| 5,900,726 A | 5/1999 | Brugger et al. |
| 5,902,253 A | 5/1999 | Pfeiffer et al. |
| 6,061,590 A | 5/2000 | Krivitski |
| 6,090,048 A | 7/2000 | Hertz et al. |
| 6,117,099 A | 9/2000 | Steuer et al. |
| 6,153,109 A | 11/2000 | Krivitshi |
| 6,177,049 B1 | 1/2001 | Schnell et al. |
| 6,189,388 B1 | 2/2001 | Cole et al. |
| 6,210,591 B1 | 4/2001 | Krivitshi |
| 6,221,040 B1 | 4/2001 | Kleinekofort |
| 6,308,737 B1 | 10/2001 | Krivitski |
| 6,623,443 B1 | 9/2003 | Polaschegg |
| 2001/0031222 A1 | 10/2001 | Schnell et al. |
| 2001/0050256 A1 | 12/2001 | Krivitshi |

FOREIGN PATENT DOCUMENTS

| | | |
|---|---|---|
| DE | 19537688 | 5/1996 |
| DE | 19528907 | 11/1996 |
| DE | 19541783 | 3/1997 |
| DE | 19901078 | 2/2000 |
| EP | 0018817 | 11/1980 |
| EP | 0089003 | 9/1983 |
| EP | 0097366 | 1/1984 |
| EP | 0272414 | 6/1988 |
| EP | 0590810 | 4/1994 |
| EP | 0693296 | 1/1996 |
| EP | 0693297 | 1/1996 |
| EP | 0773035 | 5/1997 |
| EP | 0835669 | 4/1998 |
| EP | 0845273 | 6/1998 |
| EP | 0900094 | 3/1999 |
| EP | 0928614 | 7/1999 |
| EP | 0943369 | 9/1999 |
| EP | 1020199 | 7/2000 |
| EP | 1044695 | 10/2000 |
| EP | 1083947 | 3/2001 |
| EP | 1106191 | 6/2001 |
| ES | 2026508 T | 5/1992 |
| GB | 2093192 | 8/1982 |
| JP | 60 190873 | 9/1985 |
| JP | 5 236990 | 9/1993 |
| SU | 521891 | 7/1976 |
| SU | 1013853 | 4/1983 |
| WO | WO 9608305 | 3/1996 |
| WO | WO 9701289 | 1/1997 |
| WO | WO 9710013 | 3/1997 |
| WO | WO 9817193 | 4/1998 |
| WO | WO 9817334 | 4/1998 |
| WO | WO 9832477 | 7/1998 |
| WO | WO 9964088 | 12/1999 |
| WO | WO 0018451 | 4/2000 |
| WO | WO 0074732 | 12/2000 |
| WO | WO 0108719 | 2/2001 |
| WO | WO 0204044 | 1/2002 |

OTHER PUBLICATIONS

Petitclerc et al.; "A Model for Non-invasive Estimation of in vivo Dialyzer Performances and Patient's Conductivity During Hemodialysis", The international Journal of Artificial Organs, vol. 16, No. 8, pp. 585-591, (1993).

Petitclerc et al.; "Non-invasive Monitoring of Effective Dialysis Dose Delivered to the Haemodialysis Patient", Nephrology Dialysis Transplantation, vol. 10, pp. 212-216, (1995).

Mercadal et al.; "Determination of Access Blood Flow from Ionic Dialysance: Theory and Validation", Kidney International, vol. 56, pp. 1560-1565, (1999).

Gambro; "FAM 10 Fistula Flow Studies and Their Interpretation", Lund Sweden, pp. 1-31, (1991).

Sherman; "Recirculation Revisited", Seminars in Dialysis, vol. 4, No. 4, pp. 221-223, (1991).
Smith et al.; "Cardiac Output Determined by the Saline Conductivity Method Using an Extraarterial Conductivity Cell", Cardiovascular Research Center Bulletin, vol. 5, No. 4, pp. 123-129, (1967).
Thomsen et al.; "Evaluation of Clinical Examination Preceding Surgical Treatment of AV Fistula Problems", Acta Chir Scand, vol. 151, pp. 133-137, (1985).
Transonic Systems, Inc., "Access Flow & Recirculation Measured During Hemodialysis", 7 pages, (1994).
Aldridge et al.; "The Assessment of Arteriovenous Fistulae Created for Hemodialysis from Pressure and Thermal Dilution Measurements", Journal of Medical Engeneering & Technology, vol. 8, No. 3, pp. 118-124, (1984).
Aldridge et al.; "Instrument Design for the Bedside Assessment of Arteriovenous Fistulae in Hemodialysis Patients", Proceedings EDTNA-ERCA, vol. 14, pp. 255-260, (1985).
Carr; "Integration of Decaying Exponential Sensor Output Signals", Sensors, pp. 28-34, (1989).
Daugirdas et al.; "The Fourth Annual Advanced Dialysis Technical Symposium", Dialysis & Transplantation, vol. 17, No. 8, pp. 432-433, (1998).
Fresenius "BTM 4008", 4 pages, (1993).
Gambro, Fistula Assessment Monitor FAM 10, 2 pages, (1985).
Gambro, Fistula Assessment Monitor FAM 10 Operator's Manual, pp. 1-17, (1985).
Gambro, "Fistula Assessment Monitor FAM 10 Service Manual", pp. 1-14, (1985).
Gani et al.; "Use of the Fistula Assessment Monitor to Detect Stenoses in Access Fistulae", American Journal of Kidney Diseases, vol. XVII, No. 3, pp. 303-306, (1991).
Greenwood et al.; "Assessment of Arteriovenous Fistulas From Pressure and Recirculation Studies: Clinical Experience in 215 Upper Limb Fistulas", Proc EDTA-ERA, vol. 22, pp. 296-302, (1985).
Greenwood et al.; "Assessment of Arteriovenous Fistulas From Pressure and Thermal Dilution Studies: Clinical Experience in Forearm Fistulae", Clinical Nephrology, vol. 23, No. 4, pp. 189-197, (1985).
Goldstein et al.; "The Assessment of Arteriovenous Fistulae From Pressure and Recirculation Studies", Proc EDTNA-ERCA, vol. 14, pp. 207-215, (1985).
Hart et al., A Noninvasive Electromagnetic Conductivity Sensor for Biomedical Applications, IEEE Transactions of Biomedical Engineering, vol. 35, No. 12, pp. 101 1-1022, (1988).
Hester et al.; "The Determination of Hemodialysis Blood Recirulation Using Blood Urea Nitrogen Measurements", American Journal of Kidney Diseases, vol. XX, No. 6, pp. 598-602, (1992).
Krämer et al.; "A Device for Control of Thermal Parameters and Recirculation Measurement in Hemodialysis", British Renal Symposium, 14 pages, (1992).
Transonic Systems, Inc., "Transonic Hemodialysis Monitor Measures Access Flow Recirculation Cardiac Output Routinely During Dialysis", ASAIO, 2 pages, (1995).
Krivitski; "Novel Method to Measure Access Flow During Hemdialysis by Ultrasound Velocity Dilution Technique", ASAIO Journal, vol. 41, pp. M741-M745, (1995).
Depner et al.; "Clinical Measurement of Blood Flow in Hemodialysis Access Fistulae and Grafts by Ultrasound Dilution", ASAIO Journal, vol. 41, pp. M745-M749, (1995).
Depner et al.; "Hemodialysis Access Recirulation Measured by Ultrasound Dilution", ASAIO Journal, vol. 41, pp. M749-M753, (1995).
Krivitski; "Theory and Validation of Assess Flow Measurement by Dilution Technique During Hemodialysis", Kidney International, vol. 48, pp. 244-250, (1995).
Krivitski; "Accuracy of Ultrasound Dilution Method to Measure Access Flow (AF) in Hemodialysis", XIII th International Congress of Nephrology, Abstract, p. 488, (1995).
Krivitski; "New Method to Measure Recirculation (Rc) and Access Flow During Hemodialysis (HD)", American Nephrology Nurses' Association 26th National Symposium Exhibitor Continuing Education Program, Abstract, (1995).

Depner; "Changes in Access Blood Flow (Qac) and Appearance of Recirculation (RC) During Hemodialysis", XIII th International Congress of Nephrology, Abstract, p. 570 (1995).
Depner; "Hemodialysis Access Recirculation Measured by Ultrasound Dilution", ASAIO Journal, vol. 41, No. 1., p. 80, (1995).
Depner; "Clinical Measurement of Blood Flow in Hemodialysis Access Fistulae and Grafts by Ultrasound Dilution", ASAIO Journal, vol. 41, No. 1., p. 80, (1995).
Transonic Systems, Inc., "Recirculation, Access Flow Measurements", pp. 19-26, (1995).
Sands et al.; "The Effect of Doppler Flow Screening Studies and Elective Revisions on Dialysis Access Failure", ASAIO Journal, pp. M524-M527, (1992).
Nosher; "Death, Taxes, and Vascular Access Dysfunction", Seminars in Dialysis, vol. 4., No. 2, pp. 67-68, (1991).
In-Line Diagnostics (brochure), "Improve the Clinical Outcome of Every Patient", 3 pages.
New Technology From In-Line Diagnostics (brochure), "Noninvasive Blood Volume Monitoring", 2 pages, (1994).
In-Line Diagnostics (brochure), "The Crit-Line System", 4 pages.
Bower et al.; "Circulatory Function During Chronic Hemodialysis", Trans. Amer. Soc. Artif. Int. Organs, vol. XV, pp. 373-377, (1969).
Aldridge; "The Use and Management of Arteriovenous Fistulae Fact and Fiction", EDTNA ERCA Journal XVII-4, pp. 29-35, (1991).
Hester et al.; "Non-invasive Determination of Recirculation in the Patient on Dialysis", ASAIO Journal, pp. M190-M193, (1992).
Hester; "Non-invasive Measurement of Recirculation in the Dialysis Patient", Abstract No. 7, 1 page, (1992).
Greenwood et al.; "Single Needle Dialysis", Journal of Medical Engineering & Technology, vol. 6, No. 3, pp. 93-98, (1982).
Konner et al.; "Transvenous Serial Xero-Arteriography: A New Non-Invasive Angiographic Method for AV-Fistulas in Haemodialysis Patients" Proc EDTA, vol. 18, pp. 305-309, (1981).
Forsberg et al.; "Quantitative Doppler and Ultrasound Measurements in Surgically Performed Arteriovenous Fistulas of the Arm", Acta Radiologica Diagnosis 21, Fasc. 6, pp. 769-771, (1980).
Schneditz et al.; "Cardiopulmonary Recirculation in Dialysis", ASAIO Journal, pp. M194-M196, (1992).
Louk et al.; "Magnetic Resonance, A New Method for Measuring Blood Flow in Hemodialysis Fistulae", Kidney International, vol. 45, pp. 884-889, (1994).
Depner et al.; "Access Flow Measurement From Recirculation of Urea During Hemodialysis During Reversed Blood Lines", J. Am Soc. Nephrol, vol. 6, p. 486, (1995).
Lindsay et al.; "Monitoring Vascular Access Flow", Advances in Renal Replacement Therapy, vol. 6, No. 3, pp. 273-277, (1999).
Lindsay et al.; "Estimation of Hemodialysis Access Blood Flow Rates by a Urea Method is a Poor Predictor of Access Outcome", ASAIO Journal, pp. 818-822, (1998).
Sternby; "Urea Sensors-A World of Possibilities", Advances in Renal Replacement Therapy, vol. 6, No. 3, pp. 265-272, (1999).
Yarar et al.; "Ultrafiltration Method for Measuring Vascular Access Flow Rates During Hemodialysis", Kidney International, vol. 56, pp. 1129-1135, (1999).
Polaschegg et al.; "On-Line Dynamic Measurement of Fistula Pressure During Haemodialysis for Detection of Access Stenosis and Bad Needle Placement", XXVI th Conference EDTNA—ERCA Journal, p. 23, (1997).
Polaschegg et al.; "Dynamic Pressure Measurement for Detection of Blood Access Stenosis", EDTNA- ERCA Journal, XXIV 4, pp. 39-44, (1998).
Polaschegg; "Pressure Drops in Cannulas for Hemodialysis", The International Journal of Artificial Organs, vol. 24, No. 9, pp. 614-623, (2001).
Lodi et al; "A Novel Model-Based Method for Monitoring the Hemodialysis Vasular Access", ASN/ISN World Congress of Nephrology, Codes: FC-Free Communication; PS-Poster Session 294A-A1513, (2001).
Frinak et al.; "Dynamic Venous Access Pressure Ratio Test for Hemodialysis Access Monitoring", American Journal of Kidney Diseases, vol. 40, No. 4, pp. 760-768, (2002).

Besarab et al.; "Utility of Intra-Access Pressure Monitoring in Detecting and Correcting Venous Outlet Stenoses Prior to Thrombosis", Kidney International, vol. 47, pp. 1364-1373, (1995).

Besarab et al.: "Effects of Systemic Hemodynamics on Flow Within Vascular Accesses Used for Hemodialysis", ASAIO Journal 2001, vol. 47, pp. 501-506, (2001).

Kleinekofort et al.; "Extracorporeal Pressure Monitoring and the Detection of Vascular Access Stenosis", The International Journal of Artificial Organs, vol. 25, No. 1, pp. 45-50, (2002).

Besarab et al.; "Detection of Access Strictures and Outlet Stenoses in Vascular Accesses", ASAIO Journal, vol. 43, pp. M543-M547,(1997).

Besarab et al.; "Simplified Measurement of Intra-Access Pressure", Journal of the American Society of Nephrology, vol. 9, pp. 284-289, (1998).

N.M. Krivitski, "Cardiac Output Measurement in Extracorporal Systems by Ultrasound Velocity Dilution," American Society for Artificial Internal Organs, 1994 Abstracts, 40$^{th}$ Anniversary Meeting Apr. 14-16, 1994, Abstract p. 82.

Jan Göthlin, et al., "A Dye-Dilution Method for the Determination of Blood Flow in Cimino-Brescia Arteriovenous Fistulae," *Investigative Urology*, vol. 15, No. 2, pp. 167-168.

R. N. Greenwood, et al, "Assessment of Arteriovenous Fistulas from Pressure and Recirculation Studies: Clinical Experience in 215 Upper Limb Fistulas," *Proc EDTA-ERA* (1985) vol. 22, pp. 296-302.

Arthur C. Guyton, *Textbook of Medical Physiology*, 1991 pp. 287-288.

M. Krämer, "Automated measurement of recirculation," *EDTNA ERCA Journal* XIX No. 2, Apr. 1993, pp. 6-9.

Nikolai M. Krivitski, "Novel Method to Measure Access Flow During Hemodialysis by Ultrasound Velocity Dilution Technique," *ASAIO Journal*, pp. M741-M745.

B.M.T. Lantz, et al., "Determination of Blood Flow Through Arteriovenous Fistulae and Shunts," *Acta Radiologica Diagnosis* 20 (1979) Fasc. 5, pp. 727-736.

Paulo Rocha, M.D., et al., "Arteriovenous Shunt Measured by Bolus Dye Dilution: Reproducibility and Comparison Between Two Injection Sites," *Catherterization and Cardiovascular Diagnosis*, vol. 11, pp. 473-481 (1985).

S. Gottlieb, et al., "Radiotracer Method for Nonsurgical Measurement of Blood Flow in Bovine Graft Arteriovenol's Fistulas," Proc. Dialysis Transplant Forum, 1976, pp. 107-108.

M. Salamon and P. Svitok, "A Low Frequency Electrodeless Conductometer for Measuring the Electrical Conductivity of Solutions," *United Kingdom Atomic Energy Authority Industrial Group Headquarters, Risley, Warrington, Lancashire* pp. 3-12 and "Summary" (1959).

International Search Report for International Application No. PCT/IB2004/000022.

An English-language Abstract of EP 1 020 199 A2.

An English-language Abstract of WO 98/17334.

P.G. Sakiewicz et al., "Introduction of a Switch that Can Reverse Blood Flow Direction On-Line During Hemodialysis," *ASAIO Journal*, vol. 46, n.4, Jul. 2000, pp. 464-468.

R.N. Greenwood et al., "Serial Blood Water Estimations and In-Line Blood Viscometry: The Continuous Measurement of Blood Volume During Dialysis Procedures," Clinical Science (1984) 66, pp. 575-583.

J.S. Gani et al., "Use of the Fistula Assessment Monitor to Detect Stenoses in Access Fistulae," Abstract, Australian Society of Nephrology, 1989, Australia.

L. Goldstein, "Assessment of Arteriovenous Fistulae From Pressure and Recirculation Studies," Abstract, p. 106, 1985, London, UK.

J.S. Gani et al., "Use of the Fistula Assessment Monitor to Detect Stenoses in Access Fistulae," *American Journal of Kidney Diseases*, vol. XVII, No. 3 Mar. 1991: pp. 303-306.

\* cited by examiner $$P_{vf} - P_v = R_v \cdot q_a - R_v \cdot q_{uf}$$

APPARATUS AND METHOD OF MONITORING A VASCULAR ACCESS OF A PATIENT SUBJECTED TO AN EXTRACORPOREAL BLOOD TREATMENT

This is a division of application Ser. No. 10/765,149, filed Jan. 28, 2004 now U.S. Pat. No. 7,172,570, which claims the benefit of priority of Italian Application No. MO2003A000018, filed on Jan. 28, 2003, and claims the benefit of U.S. provisional application No. 60/466,052, filed on Apr. 29, 2003, all of which are incorporated herein by reference.

BACKGROUND OF THE INVENTION

The invention relates to a system for monitoring vascular access in a patient undergoing extracorporeal blood treatment.

Specifically, though not exclusively, the invention can be usefully applied in the field of extracorporeal treatment for kidney failure.

Setting up an extracorporeal blood treatment, such as for example hemodialysis therapy, requires blood circulation in an extracorporeal circuit connected to the cardiovascular circuit of the patient through a vascular access.

The blood, taken from the patient and sent through an extracorporeal circuit, is subjected to a treatment, generally passing through a treatment unit (for example a dialyzer filter) and thereafter returned to the patient. The vascular access is where the blood is removed from the cardio-vascular system of the patient and returned to the system.

One of the vascular accesses most commonly used in hemodialysis therapy is the Cimino-Brescia artero-venous fistula access. Other vascular access types are known, however. For reasons of simplicity the present description will make reference to the artero-venous fistula as an example of vascular access, without excluding other types of vascular access from the claimed field of protection.

In an extracorporeal treatment the blood is usually taken from the vascular access by an arterial needle fluidly connected to the extracorporeal circuit. After having passed through the treatment unit, the blood is sent back to the vascular access through a venous needle. Generally blood circulation in the extracorporeal circuit is performed by a positive displacement pump, generally peristaltic.

One of the problems of extracorporeal blood treatment is monitoring the efficiency of the vascular access.

A parameter indicative of this efficiency is the blood flow rate which the vascular access can supply. This flow rate is usually greater than the blood flow rate through the extracorporeal circuit. For example, in normal conditions the blood flow rate at the vascular access is about 800÷1200 ml/minute, while the blood flow rate in the extracorporeal circuit varies between 100 and 700 ml/minute.

The flow rate at the vascular access can diminish due to a vascular pathology, such as, for example, a stenosis, i.e. a narrowing of the blood passage section, or for example due to a drop in cardiac output. The presence and location of a stenosis at the vascular access should be determined as soon as possible in order to prevent the stenosis degenerating into a thrombosis (occlusion of the blood vessels).

A reduced-efficiency vascular access can lead to the undesirable phenomenon of recirculation of blood during treatment. Recirculation consists in the presence during treatment of blood flow proceeding in an opposite to the desired direction, i.e. from the return zone of the treated blood (venous needle) to the supply zone of the blood to be treated (arterial needle). Flow recirculation therefore consists in return (in the extracorporeal circuit) of blood which has already been subjected to treatment, with a consequent diminution in treatment efficiency.

Various systems have been proposed for monitoring vascular access and, more generally, the cardiovascular system of a patient subjected to extracorporeal blood treatment.

EP 1 044 695 A2 teaches a method for determining the blood flow rate in a vascular access during hemodialysis treatment. The method varies the blood flow rate of the extracorporeal circuit and measures the arterial and venous pressures in the extracorporeal circuit during the above-cited flow rate variations. The operations are carried out in two different conditions: first with the vascular access open, in which a part of the blood flow passes through the vascular access between the withdrawal needle and the return needle, and then when the vascular access is closed, in which the vascular access flow between withdrawal needle and return needle is zero. According to the method of EP 1 044 695 A2, vascular access blood flow rate, with the vascular access open, is judged to be equal to the blood pump flow rate at which the difference of arterial pressure (or venous pressure) in the two different situations is zero.

This method has the drawback that it is necessary to intervene mechanically on the fistula to interrupt blood flow.

WO 00/18451 teaches a method for determining the flow in a fistula of a patient using an extracorporeal blood flow circuit, such as for example a hemodialysis circuit, in which the blood flows from a withdrawal point in the fistula to a return point in the fistula. The method varies the blood flow rate in the extracorporeal circuit and takes a reading of a signal which can be correlated with the fistula flow rate downstream of the withdrawal point. The blood flow rate upstream of the withdrawal point is evaluated at equal the blood flow rate obtaining in the extracorporeal circuit when the fistula blood flow rate downstream, read with the above-described signal, is zero. WO 00/18451 includes an embodiment in which the signal which can be correlated to the fistula blood flow downstream of the withdrawal point is generated by an ultrasonic sensor which operates directly on the patient's vascular access.

The use of a sensor to directly measure the blood flow rate in the fistula tract comprised between the withdrawal needle and the return needle leads to a certain constructional complication, as well as some discomfort for the patient.

EP 1 020 199 A2 teaches a method for detecting the presence of a stenosis in a vascular access during extracorporeal blood treatment. The method includes the use of at least one pressure sensor predisposed in the extracorporeal circuit along the arterial line upstream of the blood pump. A stenosis can be calculated from the entity of the pressure pulse measured by the pressure sensor.

A pressure sensor can be placed on the arterial line too downstream of the blood pump and upstream of a dialyzer, and a further pressure sensor can be placed on the venous line downstream of the dialyzer. The method also includes a reading of the pressure pulse frequency and use of that frequency as a signal entity correction factor. The pressure pulse frequency signal can be corrected by means of a function depending on the blood pump flow rate.

The data deductible from the method described in EP 1 020 199 A2 is however limited: in particular, the method provides only a general indication of the hemodynamic state of the fistula, signalling the presence of a stenosis, but it cannot gather more detailed data, such as for example the vascular access blood flow rate or the location of any stenoses found.

U.S. Pat. No. 5,830,365 teaches a method for determining some hemodynamic parameters, among which the blood flow rate in a fistula during an extracorporeal blood treatment. The method involves the alteration of at least one chemical-physical characteristic of the blood in the venous line of the extracorporeal circuit, and recording the change which occurs in the arterial line following this alteration. The alteration can be a change in the concentration of an indicator, or a change in the temperature or pressure. In a specific embodiment use is made of a hemodialysis machine provided with a dialyzer where a dialysis solution containing an indicator flows and the concentration change of the indicator in the venous and arterial lines of the extracorporeal circuit connected to the dialyzer is registered. In the venous line the concentration of the indicator increases by effect of back-filtration through the dialyzer. In the arterial line the concentration of the indicator increases by effect of recirculation in the fistula. The change of concentration in the arterial and venous lines is read by ultrasonic sensors. Alteration (in this case the change in concentration) is performed in two stages: first when the blood flows in the normal direction through the extracorporeal circuit, then when the blood flows in the opposite direction. The method includes the use of a device for inverting the blood flow direction in the extracorporeal circuit. According to the method taught in U.S. Pat. No. 5,830,365 the change in concentration measured in the first stage enables calculation of recirculation at normal flow rate, while the change in concentration measured in the second stage enables calculation of recirculation when the flow is inverted. The two calculated values thus enable a calculation of various hemodynamic parameters among which the blood flow rate in the fistula.

However the alteration of the chemical-physical properties of the blood and the inversion of the flow during the course of extracorporeal treatment lead to various drawbacks: a constructional complication, a delay in carrying out the treatment, an invasive intervention on the blood, quite removed from the course of normal treatment.

WO 02/04044 teaches a method for identifying problems in arterial flow during an extracorporeal blood treatment in which the blood is transferred, by means of a positive displacement pump, from the vascular access of a patient to a blood treatment device through an arterial line and then sent by the treatment device to the vascular access through a venous line of the extracorporeal circuit. The method consists in measuring the amplitude of the periodic variations in pressure in the venous line induced by the rotation of the blood pump, by comparing the variations with a threshold value and generating a control signal if the threshold value is exceeded. WO 02/04044 further describes another method according to which, during a dialysis treatment, the amplitude of the periodical variations of the pressure of the dialysis fluid (and not the venous line) is measured. The result is compared with a threshold value and if the threshold value is exceeded a control signal is generated.

The methods described in WO 02/04044 are not however able to provide data relating to the blood flow rate at the vascular access.

U.S. Pat. No. 6,221,040 discloses a system for monitoring a vascular access during a dialysis treatment in which the pressures in both the arterial and venous branches of the extracorporeal blood system are monitored by pressure sensors. A computer unit generates first and second characteristic values for the integrity of the vascular access from measured arterial and venous pressures. An analyser unit analyses the integrity of the vascular access by comparing the first and second characteristic values to first and second ranges of predetermined values. Calculating a sum of the venous and arterial pressure generates the first characteristic value, and calculating a difference between the venous and the arterial pressure generates the second characteristic value.

The object of U.S. Pat. No. 6,221,040 is to provide a monitoring system that allows detection of the venous cannula slipping out of the vascular access as well as detection of a blood leak in the venous branch of the extracorporeal circuit. It is not directed to determination of fistula flow.

U.S. Pat. No. 5,866,015 and EP 0 773 035 disclose a method for determining hemodynamic parameters during an extracorporeal hemotherapy, including the steps of measuring the blood temperature in the arterial branch of the extracorporeal circuit, varying the blood flow in the extracorporeal circuit, storing the values of the extracorporeal blood flow and the measured values of the blood temperature, and determining a value of the blood flow from the stored sequence of value pairs of blood temperature and of extracorporeal blood flow, at which value, after it is exceeded, the amount of the change in the blood temperature within a specific blood flow interval is greater than a predetermined limiting value. The fistula flow is inferred from the determined blood flow value.

The method is based on the fact that the measuring curve existing in discrete measured values is able to be represented by two subfunctions, the first subfunction indicating the blood temperature as a function of the extracorporeal blood flow for blood flow values smaller than the fistula flow or equal to the fistula flow, and the second subfunction indicating the blood temperature as a function of the blood flow for blood flow values greater than or equal to the fistula flow. The intersection of the two subfunctions indicates the point where the extracorporeal blood flow equals fistula flow. Thus, from the "break point" of the characteristic function curve, i.e., from the discontinuity in the rise of the curve, the point is able to be defined where fistula recirculation begins, i.e., where blood flow equals fistula flow.

In addition to measuring temperature, the concentration of a blood constituent (hematocrit) can also be measured, as can the density, speed of sonic propagation, optical density, and conductivity or viscosity.

The blood characteristic to be measured must have a different value in the venous branch of the extracorporeal circuit than it does in the blood flowing to fistula. It is assumed that the blood characteristic, preferably the temperature, is kept constant in the venous branch of the extracorporeal circuit while the measured values are recorded. If this characteristic is not constant, a regulating device to keep the characteristic in the venous branch constant must be provided. In the case of a temperature measurement, for example, this can be realized as a temperature controller.

Another drawback of this method is that the delivery rate of blood pump, which predetermines the extracorporeal blood flow, is increased starting from a lower value to an upper limiting value which must be greater than the fistula flow to be expected. Fistula flows can only be determined within the adjustable blood flow range. Therefore the fistula flow is not determinable if it is equal to or greater than the upper limiting value of the adjustable blood flow range.

The prior art comprises the scientific publication entitled: "On-line dynamic measurement of fistula pressure during hemodialysis for detection of access stenosis and bad needle placement", Abstract from the 24th EDTNA-ERCA Conference, Prague, 5-8 Jul. 1997, page 23, authors Polaschegg, Techert and Wizemann.

According to this publication it is possible to calculate the pressure of a vascular access by measuring the pressure in an extracorporeal blood circuit connected to the vascular access, with the aim of detecting any stenoses in the access itself.

In a scientific publication entitled "Dynamic pressure measurement for detection of blood access stenosis", published in the EDTNA-ERCA Journal, 1998, XXIV, 4, on pages 39-44, authors Polaschegg, Techert and Wizemann, more detail is given on monitoring problems in a patient's vascular access. The method is based on the determination of the venous and arterial pressures (upstream of the blood pump) in an extracorporeal blood circuit connected to the vascular access to be monitored. The method comprises a preliminary stage in which, through in vitro tests in which the extracorporeal circuit is not connected to a real vascular access, fluid resistances in the arterial and venous lines of the extracorporeal circuit are calculated. During a second stage the extracorporeal circuit is connected to the real vascular access of the patient in order to initiate an extracorporeal treatment. During the extracorporeal treatment the venous and arterial pressures are calculated in the extracorporeal circuit. As the venous and arterial pressures in the extracorporeal circuit are known, as are the fluid resistances in the arterial and venous lines of the extracorporeal circuit, the pressures in the vascular access can be calculated. The dynamic measurement at different flow rates and the comparison with static measures enables stenoses at the vascular access to be identified.

The scientific publication entitled "Pressure drops in cannulas for hemodialysis", author H. D. Polaschegg, published in The International Journal of Artificial Organs, Vol. 24, No. 9, 2001, pp. 614-623, relates to a method for determining a fall in pressure in an arterial or venous line in hemodialysis, with which the vascular access pressures can be determined starting from the pressures measured in the extracorporeal circuit of the hemodialysis machine.

The scientific publication entitled "Extracorporeal pressure monitoring and the detection of vascular access stenosis", authors Kleinekofort, Kraemer, Rode and Wizemann, published in The International Journal of Artificial Organs, Vol. 25, No. 1, 2002, pp. 45-50, presents a method for identifying the presence of stenoses in a vascular access, even where the stenosis is located between the withdrawal needle and the return needle. The method comprises measuring the static pressures in the arterial and venous lines of an extracorporeal circuit and in calculating the pressures at the vascular access at the withdrawal point and the return point. These pressures, which correspond to the pressures which would be measured by two pressure sensors directly connected to the withdrawal and return needles, are used in order to identify the presence of a stenosis. A knowledge of the pressures both at the point of withdrawal and at the point of return of the vascular access provides more accurate indications and enables a first approximate localization of the stenosis, especially enabling to detect if the stenosis is in venous tract or is located between the needles.

The method described here is not however able to determine the blood flow rate in the vascular access.

The publication entitled "Utility of intra-access pressure monitoring in detecting and correcting venous outlet stenoses prior to thrombosis", in Kidney International, Vol. 47 (1995), pages 1364-1373, authors Besarab, Sullivan, Ross, Moritz, teaches a method for deriving the pressure internally of the vascular access (intra-access pressure) from the pressure measured in the hemodialysis machine, as a function of the type of needle used, the blood flow rate of the hemodialysis machine, and the hematocrit of the blood. Other methods for determining the pressure at the vascular access are cited or described in the following publications:

"Detection of access strictures and outlet stenoses in vascular accesses. Which test is best?", in ASAIO Journal, 1997, Vol. 43: pages M543-M547, authors Besarab, Lubkowski, Frinak, Ramanathan, Escobar;

"Simplified measurement of intra-access pressure", in Journal of the American Society of Nephrology, 1998, Vol. 9, pages 284-289, authors Besarab, Frinak, Sherman, Goldman, Dumpler, Devita, Kapoian, Al-Saghir, Lubkowski;

"Effect of systemic hemodynamics on flow within vascular accesses used for hemodialysis", in ASAIO Journal 2001, Vol. 47, pages 501-506, authors Besarab, Lubkowski, Vu, Aslam, Frinak;

"Dynamic venous access pressure ratio test for hemodialysis access monitoring", in American Journal of Kidney Disease, Vol. 40, No 4 (October), pages 760-768, 2002, authors Frinak, Zasuwa, Dunfee, Besarab, Yee.

An abstract entitled "A novel model-based method for monitoring the hemodialysis vascular access", published in the Journal of the American Society of Nephrology, 2001, Vol. 12, N. A1513, pages 294A-295A, authors Lodi, Monari, Fava, Paolini, Grandi, Galato, Cavalcanti, cites a mathematical model based on the hemodynamic description of the vascular access which enables the arterial and venous pressures at the vascular access to be calculated and also the flow in vascular access starting from extracorporeal arterial and venous pressures. The model, which includes three parameters (resistance to flow of the anastomosis, resistance between arterial and venous access, the resistance which expresses the efficiency of venous circulation drainage), was used to analyse the data gathered during a normal hemodialysis therapy operation. The abstract states that the extracorporeal venous and arterial pressures were measured after having set four different flow rates on the blood pump and that the above-cited parameters included in the mathematical model were calculated using the mathematical model.

SUMMARY OF THE INVENTION

The present invention provides a system for controlling vascular access adequacy during an extracorporeal blood treatment.

An aim of the invention is to enable calculation of some hemodynamic parameters at the vascular access. Knowledge of these parameters enables both regulation of the blood pump flow rate operation in the extracorporeal circuit and intervention in case of detection of a pathological situation in the vascular access.

A further aim of the invention is to enable evaluation of the blood flow circulating in the vascular access of a patient during an extracorporeal blood treatment.

A further aim of the invention is to make available a system for evaluating vascular hydraulic resistance in various tracts of the patient's vascular system. In particular, an aim of the invention is to evaluate vascular resistance upstream of the blood withdrawal zone from the vascular access, downstream of the blood return zone, and in the tract of vascular access comprised between the withdrawal zone and the return zone.

An advantage of the invention is that it provides indicative values of the efficiency of the vascular access simply, automatically, using devices (such as for example pressure transducers, blood pump, drainage pump) which are normally already present in machines for extracorporeal blood treatment. A further advantage is that the invention enables monitoring of the vascular access at any time during the extracorporeal blood treatment.

A further advantage of the invention is that the monitoring procedure does not cause extra stress to the patient. The procedure can be carried out by means of variations in the blood pump or the drainage pump flow rates, or both, within flow rate intervals which are normally compatible with the extracorporeal treatment the patient undergoes. The intervals can be those normally used during the course of therapy.

These aims and others besides are all attained by the invention as it is characterised in one or more of the appended claims.

In a special function of the invention, a mathematical model is used which contains at least two parameters in which a first parameter relates to the hemodynamics of the vascular access, and a second parameter relates to the blood flow rate in the extracorporeal circuit.

The mathematical model comprises a third parameter relating to at least one blood characteristic: this characteristic can be any physical, chemical or physical-chemical property thereof which characterises the blood in a vessel and which can be related to the blood flow rate in that vessel. A peculiarity of the invention is that the mathematical model used describes the relationship between the selected blood property (physical, chemical or physical-chemical) and the blood flow rate in the vessel. In particular the mathematical model describes the relationship in the vascular access. For example, the mathematical model can describe the fluid-dynamic situation of the vascular access; the model can describe a relationship between the difference of pressure at two points of the vascular access and the flow rate crossing the points. Apart from the pressure it is also possible to select other properties (physical, chemical or physical-chemical) of the blood which are influenced by the flow rate, such as, for example: the difference in induced potential, speed of sound, optical characteristics, temperature, concentration of an indicator, and so on.

According to the invention, the monitoring of the vascular access is performed by varying the flow rate of at least one fluid (for example blood or the product of ultrafiltration), which runs either in the extracorporeal circuit or in at least one hydraulic line (for example an ultrafiltration line) connected to the extracorporeal circuit.

The monitoring can be carried out by varying both the above-cited flows.

The monitoring determines the values of at least one characteristic of the blood, in at least one zone of the blood circulation path, and at least two different values of the flow rate of the fluid.

As mentioned above, the cited characteristic of the blood can be a physical, chemical or chemical-physical one. In an embodiment of the invention, among the various characteristics of the blood that depend on blood flow, the selected characteristic to be used is the pressure.

The monitoring procedure involves calculating one or more of the hemodynamic parameters of the vascular access contained in the mathematical model, using the values of the blood characteristic determined previously during the course of the procedure.

In an embodiment of the invention, a multiplicity of values of the blood characteristic is determined; then the said hemodynamic parameters are calculated, by means of the mathematical model, using approximation algorithms (of known type). The algorithms can be chosen, for example, from those which enable determination of the value of the hemodynamic parameter, by virtue of which the blood characteristic values calculated using the mathematical model, at different flow rate values, are those which are closest to the blood characteristic values which were previously determined during the course of the procedure, at the same flow rate values.

In an embodiment of the invention, the mathematical model used is descriptive of the pressure variation at the vascular access: it comprises at least one hemodynamic parameter relative to at least one characteristic of the vascular access; at least one parameter relative to the blood characteristic; and at least one parameter relative to the blood flow rate in the extracorporeal circuit.

The hemodynamic parameter can be relative to at least one of the following characteristics of the vascular access: the blood flow rate upstream of a withdrawal zone of the blood from the access, the blood flow rate between the withdrawal zone and a blood return zone at the access, the blood flow rate downstream of the blood return zone, the vascular hydraulic resistance upstream of the blood withdrawal zone from the access, the vascular hydraulic resistance between the blood withdrawal zone and the blood return zone, and the vascular hydraulic resistance downstream of the blood return zone.

In a further embodiment of the invention, the monitoring procedure includes determining the values assumed by the blood characteristic in at least two zones of the blood circulation path (where the blood circulation path comprises both the intracorporeal circuit and the extracorporeal circuit) and at least two different flow rate values of one fluid (blood or the product of ultrafiltration).

In a further embodiment of the invention, the monitoring procedure includes determining the values assumed by the blood characteristic in at least one zone of the blood circulation path and at least two different flow rate values of two fluids (blood and the product of ultrafiltration).

In a further embodiment of the invention, the monitoring comprises a measuring stage of a blood characteristic, in a zone of the extracorporeal circuit arranged downstream of the blood withdrawal zone, or in a zone arranged upstream of the blood return zone, or in both above zones. The monitoring includes determining the blood characteristic in the vascular access, in the withdrawal zone, or in the return zone, or in both zones, by means of one or more mathematical models describing the variation of the said blood characteristic between the zones of withdrawal and return in the vascular access and the measuring zones in the extracorporeal circuit. The mathematical models can be, in particular, models descriptive of the variation of the said blood characteristic in the passage through the arterial or venous needles. In an embodiment of the invention, these mathematical models comprise at least one parameter which is relative to the blood flow, or at least one parameter relative to the hematocrit of the blood, or both said parameters. In particular the mathematical models can be represented by one or more interpolating formulas of experimental data; the formulas can be, for example, second-order polynomials with one or more parameters chosen between the flow rate and the hematocrit of the blood.

In a special operation of the invention, at regular time intervals the monitoring procedure determines the values assumed by the blood characteristic in at least one zone of the blood circulation path during the flow rate change, evaluates the variation of the blood characteristic, selects the values assumed by the blood characteristic when the variation has exceeded a threshold limit value, and uses the selected values to calculate the value of the blood characteristic at the vascular access.

In a further special operation of the invention, at regular time intervals the monitoring procedure determines the values of the blood characteristic in two different zones of the blood circulation path during flow rate change, compares the variation of the blood characteristic detected in a first zone of the blood circulation path and the variation of the characteristic detected in a second zone thereof, selects the values of the blood characteristic when the difference between the variations has exceeded a threshold limit value, and uses the selected values in calculating the value of the blood characteristic at the vascular access.

In another characteristic of the invention, in calculating the value of the characteristic of the vascular access, the monitoring procedure considers the values of the blood characteristic in a stationary blood flow situation, i.e. after having kept the flow rate constant for a determined period of time.

The monitoring procedure is applied by means of a machine for blood treatment in an extracorporeal circuit, in particular for a machine for treatment of kidney failure, predisposed to perform one or more of the following therapies: hemodialysis, hemofiltration, hemodiafiltration, pure ultrafiltration, plasmapheresis.

The machine is provided with a timer for carrying out the monitoring procedure at least once during the extracorporeal treatment.

The monitoring procedure can be initiated on command of an operator, or automatically at a predetermined moment during the treatment.

The extracorporeal circuit can be included in the complex of fluid distribution lines, of the disposable type, normally removably associated and used in a machine for treatment of renal failure.

The machine is normally equipped with pressure transducers operating in the blood withdrawal line, before the blood pump, and in the blood return line, after the blood treatment unit.

Further characteristics and advantages of the present invention will better emerge from the detailed description that follows, of a specific embodiment of the invention, illustrated purely in the form of a non-limiting example in the figures of the drawings.

BRIEF DESCRIPTION OF THE DRAWINGS

The description will be made herein below with reference to the appended figures of the drawings, here given by way of non-limiting illustration, in which.

DETAILED DESCRIPTION

Figure 1:
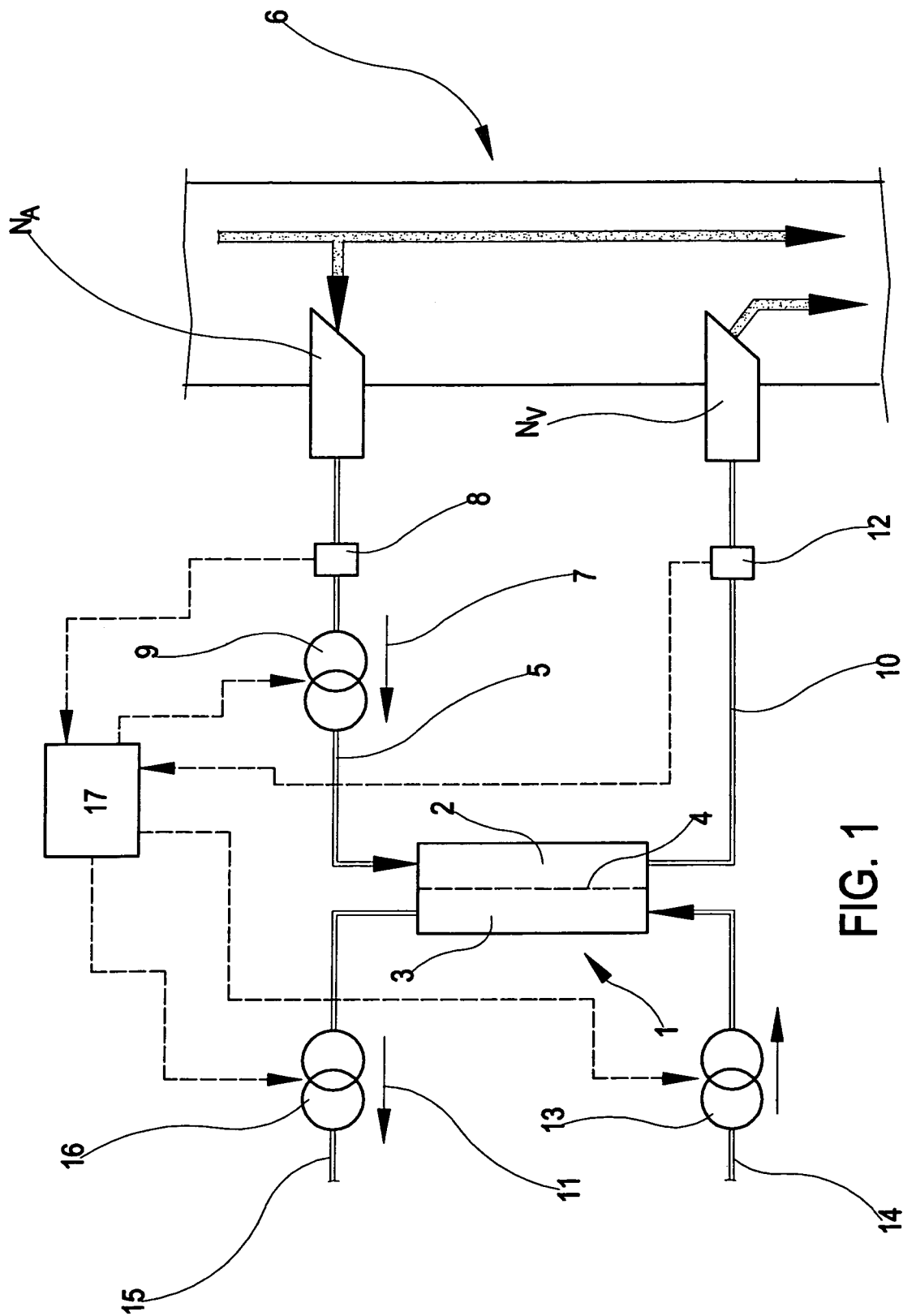
FIG. 1 is a diagram of a machine for an extracorporeal blood treatment provided with a monitoring device of the vascular access according to the invention.

The machine illustrated in FIG. 1 is a machine for hemodiafiltration comprising a unit for an extracorporeal blood treatment (a filter for hemodiafiltration 1) having two chambers 2, 3 separated by a semipermeable membrane 4. A first chamber 2 has an inlet which is connected to an arterial line 5 (blood withdrawal line from the patient) of an extracorporeal blood circuit. The arterial line 5 is connectable with a vascular access 6 of a patient by means of an access tool constituted in the example by an arterial needle $N_A$. The arterial line 5 is provided with a pressure sensor 8 and a positive displacement pump 9 for blood circulation along the extracorporeal circuit in the direction of the arrow 7.

The first chamber 2 has an outlet connected to a venous line 10 (blood return line to the patient) of the extracorporeal blood circuit. The venous line 10 is connectable to the vascular access 6 of the patient by means of an access tool constituted in the illustrated embodiment by a venous needle $N_V$. The venous line 10 is provided with a pressure sensor 12.

The second chamber 3 of the filter 1 has an inlet connected to a supply line 14 of a fresh treatment fluid (dialysis liquid) and an outlet connected to a discharge line 15 of a discharge fluid (the dialysis liquid and the ultrafiltered liquid). The supply line 14 is provided with a supply pump 13 of the fresh treatment fluid. The discharge line 15 is provided with a drainage pump 16 for the circulation of the discharge fluid in the direction of the arrow 11.

The dialysis machine further comprises a control and calculation unit 17 connected to a screen and also to a keyboard through which the user communicates to the control and calculation unit the setting values for machine operation. One of the setting values which the control and calculation unit 17 receives from the user is the blood flow rate $q_b$ in the arterial blood withdrawal line 5. The control and calculation unit 17 can control the speed of the blood pump 9 in order to have the predetermined value of flow rate $q_b$. The control and calculation unit 17 can be connected to at least one measuring device, able to provide information relating to the effective blood flow rate in the arterial line. The measuring device can comprise, for example, a flowmeter, or an encoder connected to the rotor of a blood pump. The control and calculation unit 17 is further connected to the pressure sensors 8 and 12 and receives therefrom the signals indicating the detected pressure.

The control and calculation unit 17 controls the operation of the various motor devices of the machine, in particular the blood pump 9 and drainage pump 16, according to the instructions received from the user and the programmed algorithms contained in its memory.

The machine can further comprise sensors (of known type and not illustrated) for detecting the blood viscosity upstream and downstream of the treatment unit 1. The sensors can comprise, for example, measuring devices for the blood hematocrit level.

The control and calculation unit is programmed to carry out, automatically or by request of the user, a series of operations which enable the vascular access to be monitored.

Figure 2:
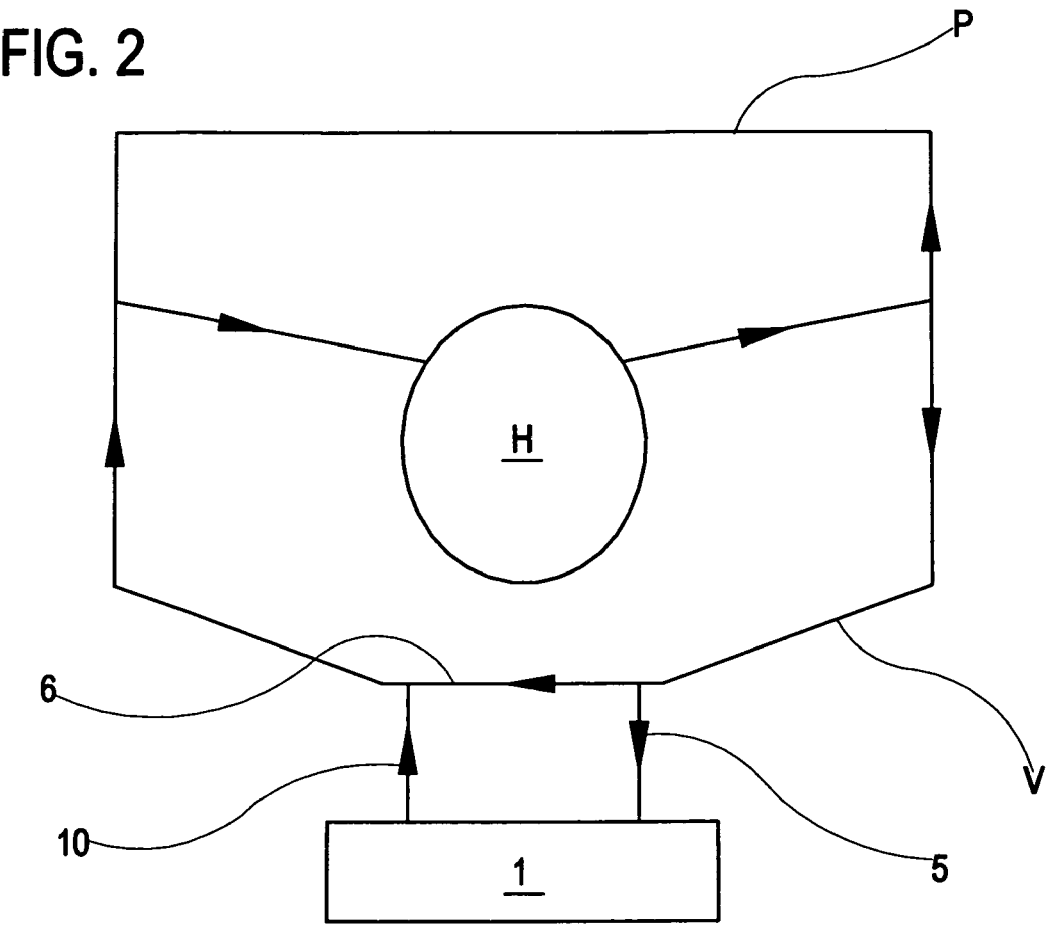
FIG. 2 is a diagram of blood flow in a patient connected up to the machine of FIG. 1.

FIG. 2 shows the patient's blood circulation subjected to extracorporeal treatment with the machine of FIG. 1. The vascular access 6, through which the extracorporeal blood circuit is connected to the cardio-vascular circuit of the patient is, in the embodiment, a fistula of the Cimino-Brescia type. In FIG. 2 H indicates the patient's heart, P denotes the pulmonary circuit, V denotes the vascular system (or systemic circuit, or intravascular circuit or intracorporeal circuit).

The arterial line 5 and the venous line 10 are connected at one end to the vascular access 6 and at the other end to the dialysis filter 1.

Figure 3:
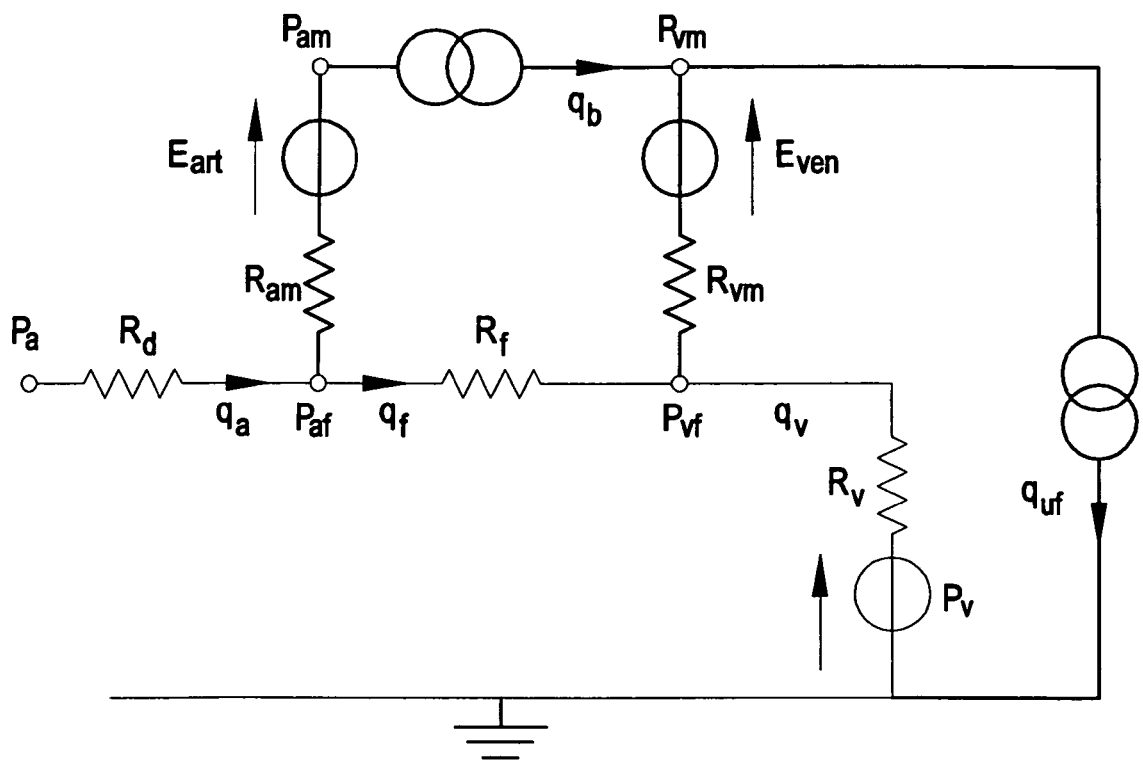
FIG. 3 is an electrical diagram which describes by analogy the circulation of extracorporeal and intracorporeal blood of the patient subjected to the extracorporeal treatment with the machine of FIG. 1.

FIG. 3 shows an electrical diagram which, by analogy, describes the blood circulation of the patient subjected to the extracorporeal blood treatment.

The legend to FIG. 3 is as follows.

Quantities Controlled by the Control Unit 17:
$q_b$ blood pump flow rate [ml/min]
$q_{uf}$ ultrafiltration flow rate [ml/min]

Known Quantities (Measurable Directly or Indirectly or Determinable from Indirect Measurements Using a Mathematical Model):

$P_{am}$ extracorporeal arterial pressure [mmHg]

$P_{vm}$ extracorporeal venous pressure [mmHg]

$E_{art}$ hydrostatic pressure related to the height level difference between the pressure sensor 8 in the arterial line of the extracorporeal circuit and the arterial needle $N_A$ [mmHg]

$E_{ven}$ hydrostatic pressure related to the height level difference between the pressure sensor 12 in the venous line of the extracorporeal circuit and the venous needle $N_V$ [mmHg]

$R_{am}$ hydraulic resistance of the extracorporeal arterial line [mmHg·min/ml]

$R_{vm}$ hydraulic resistance of the extracorporeal venous line [mmHg·min/ml]

$P_{af}$ vascular access arterial pressure [mmHg]

$P_{vf}$ vascular access venous pressure [mmHg]

$P_a$ mean systemic arterial pressure (MAP) [mmHg]

$P_v$ venous pressure (venous return pressure) [mmHg]

Unknown Quantities to be Determined:

$q_a$ blood flow rate at the vascular access, upstream of the arterial access [ml/min]

$q_f$ blood flow rate of artero-venous anastomosis in the vascular access tract comprised between the arterial access and the venous access, ($q_f = q_a - q_b$) [ml/min]

$q_v$ blood flow rate downstream of the venous access, ($q_v = q_a - q_{uf}$) [ml/min]

$R_d$ hydraulic resistance upstream of the vascular access [mmHg·min/ml]

$R_f$ hydraulic resistance between the arterial access and the venous access [mmHg·min/ml]

$R_v$ hydraulic resistance downstream of the vascular access [mmHg·min/ml]

In the diagram of FIG. 3 the extracorporeal blood circuit is traced in bold line, while the intracorporeal circulation in the vascular access is drawn in thin line.

The nodes where the extracorporeal circuit meets with the vascular access are the zones where pressures $P_{af}$ e $P_{vf}$ are determined (either directly measured or calculated).

Various methods are known, based on mathematical models, for calculating pressures $P_{af}$ e $P_{vf}$ from known pressures $P_{am}$ e $P_{vm}$ in the extracorporeal circuit. Some of these methods are described in the scientific publications cited in the present description. Herein below details will be given of a method founded on a new mathematical model based on the electrical diagram represented in FIG. 3.

In the following a mathematical model is shown, also based on the electrical diagram of FIG. 3, representative of the hemodynamics of the vascular access of an extracorporeal blood circuit in which the blood is removed from the patient through an arterial needle, is made to circulate through the extracorporeal circuit and is returned through a venous needle.

The mathematical model describes the variation of pressure in the vascular access as a function of the blood flow rate.

The mathematical model is expressed in the following three equations which can be derived from the electrical diagram represented in FIG. 3.

$$q_a = \frac{P_a - P_{af}}{R_d}$$

$$P_{af} - P_{vf} = R_f \cdot (q_a - q_b)$$

$$P_{vf} - P_v = R_v \cdot (q_a - q_{uf})$$

where, as mentioned herein above, the symbols have the following meanings:

$q_a$=blood flow rate at the vascular access 6 (fistula), upstream of the withdrawal point of the arterial needle $N_A$ $q_b$=blood flow rate in the arterial line 5 of the extracorporeal circuit $P_a$=mean systemic arterial pressure measured at patient's arm $P_{af}$=arterial pressure in the vascular access 6, i.e. the pressure in the vascular access (in the embodiment, with a Cimino-Brescia fistula, this is a tract of arterialized vein) at the point of withdrawal of the arterial needle $N_A$ $R_d$=resistance of the tract of arterialised vein comprised between the anastomosis and the point of withdrawal of the arterial needle $N_A$ $P_{vf}$=venous pressure in the vascular access 6, i.e. the pressure in the fistula at the return point of the venous needle $N_V$ $R_f$=vascular resistance of the tract of fistula comprised between the two needles $N_A$ and $N_V$ and representing the resistance between the two points at which $P_{af}$ and $P_{vf}$ are determined $P_v$=venous pressure of the blood in the distal venous branch; the Pv value can be unknown during the extracorporeal treatment; in this case it can be placed at a constant physiological value (e.g. $P_v$=0)

$R_v$=vascular resistance in the venous branch of the blood return zone at the zone where venous pressure $P_v$ is evaluated; where $P_v$=0, the resistance $R_v$ represents total venous resistance, i.e. the vascular resistance met by the blood in returning from the venous needle $N_V$ to the heart H, which constitutes an indicative value of the drainage efficiency of the venous circulation $q_{uf}$=ultrafiltration flow rate (in case of hemodiafiltration, $q_{uf}$ is the difference between the discharge fluid flow rate in the discharge line 15 and the fresh dialysis fluid flow rate in the supply line 14).

The pressures in the above-indicated mathematical model relate to atmospheric pressure. The arterial and venous pressures $P_{af}$ and $P_{vf}$ in the vascular access are measurable directly, for example using pressure sensors operating directly on the vascular access 6 in proximity or internally of the arterial and venous needles $N_A$ e $N_V$.

As previously mentioned, the pressures $P_{af}$ and $P_{vf}$ are also determinable indirectly using a mathematical model which includes, among its parameters, pressures $P_{am}$ and $P_{vm}$ (arterial and venous pressures) measured in the extracorporeal circuit by the pressure sensors 8 and 12. The prior art comprises various mathematical models usable for calculating pressures $P_{af}$ and $P_{vf}$ when pressures $P_{am}$ and $P_{vm}$ are known. Some of the above-cited prior art contains examples of so-usable mathematical models. There follows a further example of a mathematical model usable for determining the intravascular pressures of the blood starting from the easily-measurable values of the extracorporeal blood pressures.

Determination of $P_{af}$ and $P_{vf}$ with $P_{am}$ and $P_{vm}$ Known.

The mathematical model used comprises the two equations which can be derived from the electrical diagram of FIG. 3:

$$P_{af} = P_{am} + E_{art} + R_{am} \cdot q_b$$

$$P_{vf} = P_{vm} + E_{ven} - R_{vm} \cdot (q_b - q_{uf})$$

Resistances $R_{am}$ and $R_{vm}$ can be considered equal, with satisfactory approximation, to the hydraulic resistance of the arterial needle $N_A$ and, respectively, the venous needle $N_V$; it is therefore assumed for the sake of simplicity that the whole drop in pressure in the arterial and venous lines is concentrated at the respective needles.

To calculate the hydraulic resistance R of a needle, the following mathematical model is used: it makes use of an equation which connects the hydraulic resistance of the needle with the blood flow rate and the blood hematocrit.

$$R = (A_2 \cdot q_b^2 + A_1 \cdot q_b + B_2 \cdot Hct^2 + B_1 \cdot Hct + B_0) \cdot R_{Poiseuille}$$

where $q_b$ = blood flow rate $Hct$ = blood hematocrit $$R_{Poiseuille} = \frac{8 \cdot L}{\pi \cdot r^4}$$

$L$ = length of needle $r$ = radius of internal section of the needle $R_{Poiseuille}$ is the theoretical hydraulic resistance calculated using the Hagen-Poiseuille law for a liquid with viscosity equal to one.

$A_2, A_1, B_2, B_1$ and $B_0$ are coefficients characteristic of each needle, the value being obtained by means of experimental preliminary laboratory testing, by measuring the fall of pressure through the needle with different blood and hematocrit flow rates. In experimental tests the flow rate was varied within a range from 0 to 500 ml/minute, while the hematocrit was varied within a range from 30 to 45%. The coefficients differ for a same needle according to blood flow direction, that is whether the needle is used as an arterial needle or as a venous needle. These preliminary in vitro tests serve to experimentally characterise the needles which will then be used for the extracorporeal blood treatment. The tests include simulation of the extracorporeal treatment (for example dialysis) using a machine for performing the treatment (for example a dialysis machine) with an extracorporeal circuit lacking the device for effecting the treatment (for example lacking a dialyzer filter), causing bovine blood to circulate, exiting from a container and returning thereto. The blood is kept at a constant temperature of 37° C. The blood hematocrit is measured. The machine and the circuit used in the tests can be the same as those illustrated in FIG. 1.

At intervals of about 1 minute the blood pump flow rate $q_b$ is changed, starting from a zero flow rate $q_{b0}$=0 ml/minute and increasing it by 50 ml/minute up to a maximum flow rate of 500 ml/minute ($q_{b1}$=50 ml/min, $q_{b2}$=100 ml/min, ..., $q_{bi}$=i·50 ml/min, ..., $q_{b10}$=500 ml/min). In general, the flow rate $q_b$ assumes N different values $q_{bi}$ with i=0, 1, 2, ..., N (N≧3).

At each interval pressures $P_{ami}$ and $P_{vmi}$ are measured using the pressure sensors placed along the extracorporeal circuit. From each pressure value measured, $P_{ami}$ and $P_{vmi}$, we subtract the hydrostatic pressure due to the different blood level in the container with respect to the point of measurement of the pressure on the machine. From pressures $P_{ami}$ and $P_{vmi}$ we can deduce the pressure falls of the corresponding needles $\Delta P_{ai}$ and $\Delta P_{vi}$, with i=0, 1, 2, ..., N (N≧3).

The same operations are repeated, each time controlledly changing the value of the hematocrit in the bovine blood. The blood flow rate values $q_b$ are the same each time, i.e. $q_b = q_{bi}$, with i=0, 1, 2, ..., N.

The hematocrit can be varied by dilution with physiological solution (in this case the hematocrit diminishes each time). For each series of operations the value of the hematocrit is measured. Purely by way of an example, the operations can be performed with the following hematocrit values: about 44%, about 42%, about 40%, about 38%, about 36%, about 34%, about 32%. In general the value of the hematocrit Hct assumes M different $Hct_j$ values with j=1, 2, ..., M (with M≧2).

Thus, for each needle we obtain a number N·M of values $\Delta P_{aij}$ and $\Delta P_{vij}$ with i=0, 1, 2, ..., N (with N≧3) e j=1, 2, ..., M (with M≧2).

A processor calculates the hydraulic resistances of the needle, normalised with respect to the Poiseuille resistance, for one of the hematocrit values (for example Hct=$Hct_1$) according to the equation:

$$R_{ai1} = \frac{\Delta P_{ai1}}{q_{bi}} \cdot \frac{1}{R_{Poiseuille}}$$

$$R_{vi1} = \frac{\Delta P_{vi1}}{q_{bi}} \cdot \frac{1}{R_{Poiseuille}}$$

in which $R_{ai1}$=resistance of the arterial needle at flow rate $q_b = q_{bi}$ and with hematocrit Hct=$Hct_1$ $R_{vi1}$=resistance of the venous needle at flow rate $q_b = q_{bi}$ and with hematocrit Hct=$Hct_1$ $\Delta P_{ai1}$=pressure drop on the arterial needle at flow rate $q_b = q_{bi}$ and with hematocrit Hct=$Hct_1$.

$\Delta P_{vi1}$=pressure drop on the venous needle at flow rate $q_b = q_{bi}$ and with hematocrit Hct=$Hct_1$.

Hence we obtain two series of values $R_{ai1}$ and $R_{vi1}$ of resistances (one arterial and the other venous) corresponding to a determined hematocrit value (in the example Hct=$Hct_1$), with i=0, 1, 2, ..., N, with N=number of times we determine $\Delta P_{ai1}$ and $\Delta P_{vi1}$ at different flow rates $q_{bi}$.

Each of the two series of values ($R_a$ and $R_v$) is interpolated by the processor using a second-order polynomial:

$$R = A_2 q_b^2 + A_1 q_b + b_1$$

and we thus obtain, for each type of needle, a pair of coefficients $A_2$ and $A_1$ for each flow direction (i.e. we obtain a pair of coefficients which characterise the arterial needle and a pair of coefficients which characterise the venous needle). Coefficient $b_1$ depends on the blood hematocrit value.

Coefficients $B_2, B_1$ and $B_0$ are obtained as follows.

Let us for a moment consider only one blood flow direction through the needle: for example, the arterial needle.

The processor also calculates the resistances $R_a$ of the arterial needle for the other hematocrit values Hct=$Hct_j$ (j= 2, ..., M), at different blood flow rates $q_b = q_{bi}$ (i=0, 1, 2, ..., N), thus obtaining various series of values:

$$R_{aij} = \frac{\Delta P_{aij}}{q_{bi}} \cdot \frac{1}{R_{Poiseuille}}$$

These values of $R_a$ are interpolated, for each hematocrit value Hct, according to the blood flow rate $q_b$, using a second order polynomial:

$$R_{ai2}=A_2q_b^2+A_1q_b+b_2 \text{ for Hct=Hct}_2$$

$$R_{ai3}=A_2q_b^2+A_1q_b+b_3 \text{ for Hct=Hct}_3$$

...

$$R_{aiM}=A_2q_b^2+A_1q_b+b_M \text{ for Hct=Hct}_M$$

with i=0, 1, 2, . . . , N (with N≧3), in order to obtain a series of values $b_j$ (j=1, 2, . . . , M).

In substance, exemplifying the above-mentioned process step by step, for j=1 the processor interpolates values $R_{ai1}$ (for Hct=Hct$_1$) according to the equation $$R_{ai1}=A_2q_b^2+A_1q_b+b_1$$

and thus determines $b_1$.

Then it interpolates values $R_{ai2}$ for j=2 (for Hct=Hct$_2$) following the equation $$R_{ai2}=A_2q_b^2+A_1q_b+b_2$$

and determines $b_2$, and so on up until j=M, thus obtaining M values of $b_j$.

At this point the processor makes a further interpolation, using the values of $b_j$ according to the equation $$b=B_2Hct^2+B_1Hct+B_0$$

and thus determines coefficients $B_2$, $B_1$ and $B_0$.

The same series of interpolations is effected using the data relating to the venous needle.

Hereafter we report some examples of values of the coefficients $A_2$, $A_1$, $B_2$, $B_1$ and $B_0$ experimentally obtained.

With a needle having the following characteristics: gauge=15 (internal diameter=1.6 mm), length=28 mm, the following is obtained:

$A_2$(arterial)=−0.00004, $A_1$(arterial)=0.0351, $B_2$(arterial)=0.0192, $B_1$(arterial)=−0.9398, $B_0$(arterial)=21.059, $R_{Poiseuille}$=0.022

$A_2$(venous)=−0.000026, $A_1$(venous)=0.0266, $B_2$(venous)=0.0403, $B_1$(venous)=−2.2937, $B_0$(venous)=41.969, $R_{Poiseuille}$=0.022

With a needle having the following characteristics: gauge=16 (internal diameter=1.4 mm), length=33 mm, the following is obtained:

$A_2$(arterial)=−0.00004375, $A_1$(arterial)=0.0309, $B_2$(arterial)=0.0081, $B_1$(arterial)=−0.3226, $B_0$(arterial)=8.3882, $R_{Poiseuille}$=0.0442

$A_2$(venous)=−0.00002875, $A_1$(venous)=0.0193, $B_2$(venous)=0.0037, $B_1$(venous)=0.0487, $B_0$(venous)=1.4565, $R_{Poiseuille}$=0.0442.

The control and calculation unit 17 memory is preloaded with the coefficient values $A_2$, $A_1$, $B_2$, $B_1$ and $B_0$ of the most commonly used needles (the memory contains two series of coefficients for each needle, one for each blood flow direction, i.e. a series relating to a needle's use as an arterial needle and as a venous needle). The control and calculation unit 17 recognises the needle used in the extracorporeal treatment time by time and consequently in the calculation of $P_{af}$ and $P_{vf}$ uses the coefficients relating to the needle being used. Recognition of the needle can be automatic (for example by means of an identification system associated to the needle) or can be user-guided.

Thus a mathematical model is defined, usable by the control and calculation unit 17 for determining the pressures in the vascular access by measuring the pressure in the extracorporeal circuit.

Herein below some operative methods are defined by means of which a processor in the control and calculation unit 17 of the machine can monitor the vascular access during an extracorporeal treatment.

First Monitoring Procedure.

In this first operative mode $q_b$ is varied at $q_{uf}$=constant (=0), while $P_{am}$ and $P_{vm}$ are measured.

The operative mode is now described step by step.

a. Determine values $P_{af1}$ and $P_{vf1}$ of the arterial pressure and, respectively, the venous pressure in the vascular access (fistula) at a known blood pump flow rate $q_{b1}$.

b. Save and store values $q_{b1}$, $P_{af1}$ and $P_{vf1}$ in a memory.

c. Change the blood pump flow rate to a known value $q_{b2}$. At the same time the ultrafiltration flow rate $q_{uf}$ is kept constant.

d. Keep the blood pump flow rate at $q_{b2}$ for a determined period of time (for example about ten seconds) to let the system become stable.

e. Determine values $P_{af2}$ and $P_{vf2}$ of the arterial pressure and, respectively, of the venous pressure in the vascular access (fistula) at blood pump flow rate $q_{b2}$.

f. Save and store values $q_{b2}$, $P_{af2}$ and $P_{vf2}$.

g. Steps c-f can be repeated for a desired number of times so as to save and store a series of values $q_{bi}$, $P_{afi}$, $P_{vfi}$, with i=1, 2, 3, . . . , N, where N is an integer number greater than 1.

h. Calculate $R_f$ and $q_a$ using the values stored in the memory and the mathematical model expressed by the equation $$P_{af}-P_{vf}=R_f(q_a-q_b)$$

i. Save and store the values calculated for $R_f$ and $q_a$.

j. Calculate $R_v$ using at least a part of the stored values and the mathematical model expressed by the equation $$P_{vf}-P_v=R_v\cdot(q_a-q_{uf})$$

k. Save and store the calculated value for $R_v$.

l. Calculate $R_d$ using at least a part of the stored values and the mathematical model expressed in the equation $$q_a = \frac{P_a - P_{af}}{R_d}$$

where $P_a$ (mean systemic arterial pressure or MAP) is measured at the patient's arm in known ways and the measured value of $P_a$ is transmitted to the control and calculation unit 17.

m. Save and store the value calculated for $R_d$.

The calculation of $R_f$ and $q_a$ in point h can be done in the following way.

The stored values of $q_{bi}$, $P_{afi}$ and $P_{vfi}$, with i=1, 2, . . . , N (with N≧2), are introduced into the equation $$P_{af}-P_{vf}=R_f(q_a-q_b)$$

so as to obtain a system of N equations with 2 unknowns $q_a$ and $R_f$.

$$\Delta P_{f1} = R_f \cdot (q_a - q_{b1})$$

$$\Delta P_{f2} = R_f \cdot (q_a - q_{b2})$$

...

$$\Delta P_{fN} = R_f \cdot (q_a - q_{bN})$$

where $\Delta P_{fi} = P_{afi} - P_{vfi}$ with $i = 1, 2, \ldots, N$ ($N \geq 2$)

The unknown quantities $q_a$ and $R_f$ can be determined by calculating the optimal solution of the above-indicated equation system.

If $N=2$ the system has an analytical solution.

If $N>2$ the two unknowns $q_a$ and $R_f$ can be determined using an optimisation algorithm.

For example the processor calculates the two values, one $q_a$ and the other $R_f$, for which the corresponding values of $\Delta P_f$ calculated by the above-indicated system of equations are the closest to the $\Delta P_{fi}$ values previously-determined at point e.

The following calculation procedure can be used. Using the values stored in memory, $q_{bi}$, $P_{afi}$ and $P_{vfi}$, by means of a mathematical interpolation algorithm previously stored in memory the processor determines a linear equation which approximates the relation between $\Delta P_f$ and $q_b$. Then the value of $q_b$ at $\Delta P_f = 0$ is calculated, using the above-indicated linear equation. The value of $q_b$ at $\Delta P_f = 0$ is assumed to be equal to the flow rate $q_a$ of the vascular access. The value of $q_a$ thus determined is stored in memory. Further, the processor calculates the value assumed by $\Delta P_f$ at $q_b = 0$, once more using the same linear equation. The value of $\Delta P_f$ at $q_b = 0$ is assumed to be equal to the product of $R_f \cdot q_a$. At this point, using the previously-stored value of $q_a$ the value of $R_f$ can be calculated with a simple quotient.

Graph $\Delta P_f - q_b$ of FIG. 2 illustrates this mode of procedure. The points in FIG. 2 represent the determined values $\Delta P_{fi}$ of $\Delta P_f$ according to the blood pump flow rate $q_b$. The straight line interpolating the various points is the graphic representation of the linear mathematical relation which connects $\Delta P_f$ with $q_b$.

The interpolation method can be any known linear interpolation method. The straight line of interpolation intersects the horizontal axis ($q_b$) at $q_a$ and the vertical axis ($\Delta P_f$) at $R_f \cdot q_a$.

Another way of calculating $q_a$ and $R_f$ is based on the description of the relation between $q_b$ and $\Delta P_f$ using a non-linear mathematical relation (for example a polynomial of a degree greater than one), derived by the processor with an interpolation method using the values stored in the memory $q_{bi}$, $P_{afi}$ e $P_{vfi}$. After having derived this non-linear relation, the value assumed by $q_b$ at $\Delta P_f = 0$ is assumed to be equal to the flow rate $q_a$ of the vascular access. The value of $q_a$ thus determined is stored in memory. Further, the processor calculates the value assumed by $\Delta P_f$ at $q_b = 0$, using the above-cited non-linear equation as well. The value of $\Delta P_f$ at $q_b = 0$ is assumed to be equal to the product of $R_f \cdot q_a$. At this point, using the previously-stored value of $q_a$ it is possible to calculate, by a simple division, the value of $R_f$. This value represents, in the embodiment, the value of hydraulic resistance $R_f$ at point $q_b = 0$ (i.e. at zero blood flow rate in the extracorporeal circuit).

At point c., the blood pump flow rate is varied from $q_{b1}$, to $q_{b2}$, so that, in consequence of the change of flow rate $q_{b2} - q_{b1}$, the pressure difference $\Delta P_f = P_{af} - P_{vf}$ varies significantly in absolute value and sufficiently to be appreciated (for example at least 2 mmHg), i.e. so that $$|P_{f1} - \Delta P_{f2}| \geq 2 \text{ mmHg},$$

where $$\Delta P_{f1} = P_{af1} - P_{vf1} \text{ and}$$

$$\Delta P_{f2} = P_{af2} - P_{vf2}$$

The same occurs for each flow rate change from $q_{bi}$ to $q_{b(i+1)}$. The values of $q_{bi}$ are selected so that the difference between the minimum value and the maximum value of $q_{bi}$ does not exceed a predefined value (for example about 600 ml/min) in order that $q_a$ and $R_f$ can be considered as constant in the calculation with good approximation.

At point c. the ultrafiltration flow rate $q_{uf}$ is kept constant $= 0$.

At point j. the resistance $R_v$ is calculated assuming $q_{uf} = 0$. The $R_v$ stored in memory can be one of the estimated $R_{vi}$ or the mean value of the estimated $R_{vi}$.

$$R_{vi} = \frac{P_{vfi} - P_v}{q_a}$$

At point l. the resistance $R_d$ stored in the memory can be one of the $R_{di}$ calculated with equation (1) or the mean value of the calculated $R_{di}$.

$$R_{di} = \frac{P_a - P_{afi}}{q_a}$$

Second Monitoring Procedure.

In the second operative mode $q_{uf}$ is changed to $q_b = $ constant (not zero), while $P_{am}$ and $P_{vm}$ are measured.

The operative mode is now described step by step.

a. Determine values $P_{af1}$, and $P_{vf1}$, of the arterial pressure and, respectively, of the venous pressure in the vascular access (fistula) at a known ultrafiltration flow rate $q_{uf1}$ at a predetermined blood pump-flow rate $q_b$.

b. Save and store values $q_{uf1}$, $P_{af1}$ and $P_{vf1}$.

c. Change the ultrafiltration flow rate to a known value $q_{uf2}$. At the same time the blood pump flow rate $q_b$ is kept constant and equal to the initial flow rate of point a.

d. Keep the ultrafiltration pump flow rate at value $q_{f2}$ for a determined period of time (for example about ten seconds) to let the system become stable.

e. Determine values $P_{af2}$ and $P_{vf2}$ of the arterial pressure and, respectively, the venous pressure in the vascular access (fistula) at ultrafiltration flow rate $q_{uf2}$ of the blood pump.

f. Save and store values $q_{uf2}$, $P_{af2}$ and $P_{vf2}$.

g. Steps c-f can be repeated for a desired number of times so as to save and store a series of values $q_{ufi}$, $P_{afi}$, $P_{vfi}$, with $i=1, 2, 3, \ldots, N$, where N is an integer number greater than 1.

h. Calculate $q_a$ and $R_v$ using the values stored in the memory and the mathematical model expressed in the equation $$P_{vf} - P_v = R_v \cdot (q_a - q_{uf})$$

i. Save and store the values calculated for $R_v$ and $q_a$.

j. Calculate $R_f$ using at least a part of the stored values and the mathematical model expressed in the equation $$P_{af} - P_{vf} = R_f \cdot (q_a - q_b)$$

k. Save and store the calculated value for $R_f$.

l. Calculate $R_d$ using at least a part of the stored values and the mathematical model expressed in the equation $$q_a = \frac{P_a - P_{af}}{R_d}$$

m. Save and store the value calculated for $R_d$.

At point c., the ultrafiltration flow rate is changed from $q_{uf1}$ to $q_{uf2}$ so that, in consequence of the change in flow rate $q_{uf2}-q_{uf1}$, the difference of pressure $\Delta P_{vf}=P_{vf}-P_v$ significantly varies in absolute terms sufficiently to be appreciated (for example at least 3 mmHg), i.e. so that $$|\Delta P_{vf1} - \Delta P_{vf2}| \geq 3 \text{ mmHg},$$

where $$\Delta P_{vf1}=P_{vf1}-P_v \text{ and}$$

$$\Delta P_{vf2}=P_{vf2}-P_v$$

The same can be said for each flow rate change from $q_{ufi}$ to $q_{uf(i+1)}$.

At point c. the blood flow rate in the extracorporeal circuit $q_b$ is kept constant at a known value which is not zero.

At point h. the calculation of $R_v$ and $q_a$ is performed in the following way.

The stored values of $q_{ufi}$, $P_{afi}$ and $P_{vfi}$, with i=1, 2, ..., N (with N≧2), are introduced in the equation $$P_{vf}-P_v=R_v \cdot (q_a-q_{uf})$$

so as to obtain a system of N equations with 2 unknown quantities $q_a$ and $R_v$.

$$P_{vf1}-P_v=R_v \cdot (q_a-q_{uf1})$$

$$P_{vf2}-P_v=R_v \cdot (q_a-q_{uf2})$$

$$P_{vfN}-P_v=R_v \cdot (q_a-q_{ufN})$$

The unknown quantities $q_a$ and $R_v$ can be determined by calculating the optimal solution of the above-indicated equation system.

If N=2 the system has an analytical solution.

If N>2 the two unknowns $q_a$ and $R_v$ can be determined using an optimization algorithm.

A calculation procedure which can be used is the following. Using the values stored in memory, $q_{ufi}$ and $P_{vfi}$, the processor determines, by means of a mathematical interpolation algorithm previously stored in memory, a linear equation which approximates the relation between $\Delta P_{vf}$ and $q_{uf}$ where $\Delta P_{vf}=P_{vf}-P_v$. Then the value assumed by $q_{uf}$ at $P_{vf}-P_v=0$ is calculated, using the above-indicated linear equation. The value of $q_{uf}$ at $\Delta P_{vf}=0$ is assumed to be equal to the flow rate $q_a$ of the vascular access. The value of $q_a$ thus determined is stored in memory. Further, the processor calculates the value assumed by $\Delta P_{vf}$ at $q_{uf}=0$, once more using the same linear equation. The value of $\Delta P_{vf}$ at $q_{uf}=0$ is assumed to be equal to the product of $R_v \cdot q_a$. At this point, using the previously-stored value of $q_a$ the value of $R_v$ can be calculated by a simple division.

Figure 5:
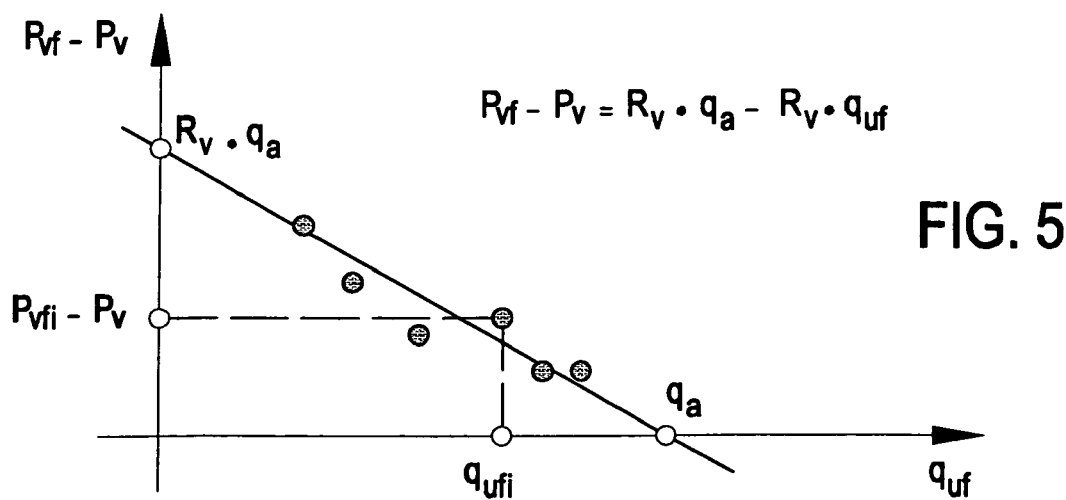
FIG. 5 is a diagram of the relation between $(P_{vf}-P_v)$ e $q_{uf}$, where $(P_{vf}-P_v)$ is the difference between the venous pressure in the vascular access $P_{vf}$ and the systemic venous pressure $P_v$, and $q_{uf}$ is the ultrafiltration flow rate.

The plot of $\Delta P_{vf}$ as a function of $q_{uf}$ in FIG. 5 illustrates this mode of procedure. The points in FIG. 5 represent the determined values $\Delta P_{vfi}=P_{vfi}-P_v$ of $\Delta P_{vf}$ as functions of the ultrafiltration pump flow rate $q_{uf}$. The straight line interpolating the various points is the graphic representation of the linear mathematical relation which connects $\Delta P_f$ with $q_{uf}$. The interpolation method can be any known linear interpolation method. The straight interpolating line intersects the horizontal axis $q_{uf}$ at $q_a$ and the vertical axis of $\Delta P_{vf}$ at $R_v \cdot q_a$.

At point j. (determination of $R_f$) the following procedure is observed.

For each of the estimated values of $P_{afi}$ and $P_{vfi}$, a corresponding value of $R_{fi}$ is calculated using the above-indicated equation, from which it is obtained:

$$R_{fi} = \frac{P_{afi} - P_{vfi}}{q_a - q_{b1}}$$

The $R_f$ value stored at point k. can be one of the calculated values for $R_{fi}$ or the mean value of the $R_{fi}$ values.

At point l. (determination of $R_d$) the following procedure is observed.

For each of the estimated values of $P_{afi}$, a corresponding value of $R_{di}$ is calculated using the above-indicated equation:

$$R_{di} = \frac{P_a - P_{afi}}{q_a}$$

The $R_d$ value stored at point l. can be one of the calculated values $R_{di}$ or the mean value of the $R_{di}$ values.

Third Monitoring Procedure.

The equations which define the mathematical model of the vascular access used previously:

$$q_a = \frac{P_a - P_{af}}{R_d}$$

$$P_{af} - P_{vf} = R_f \cdot (q_a - q_b)$$

$$P_{vf} - P_v = R_v \cdot (q_a - q_{uf})$$

can be reformulated so as to evidence the dependence of $P_{af}$ and $P_{vf}$ on $P_a$, $q_b$, $q_{uf}$ and $P_v$ through the unknown parameters $R_d$, $R_f$ and $R_v$. The reformulated equations are as follow:

$$P_{af} = \frac{R_f + R_v}{R_d + R_f + R_v} \cdot P_a - \frac{R_d \cdot R_f}{R_d + R_f + R_v} \cdot q_b -$$
$$\frac{R_d \cdot R_v}{R_d + R_f + R_v} \cdot q_{uf} + \frac{R_d}{R_d + R_f + R_v} \cdot P_v$$

$$P_{vf} = \frac{R_v}{R_d + R_f + R_v} \cdot P_a + \frac{R_f \cdot R_v}{R_d + R_f + R_v} \cdot q_b -$$
$$\frac{R_v \cdot (R_d + R_f)}{R_d + R_f + R_v} \cdot q_{uf} + \frac{R_d + R_f}{R_d + R_f + R_v} \cdot P_v$$

These equations can be rewritten as reported herein below.

$$P_{af}=c_{a0} \cdot P_a + c_{a1} \cdot q_b + c_{a2} \cdot q_{uf} + (1-c_{a0}) \cdot P_v$$

$$P_{vf}=c_{v0} \cdot P_a + c_{v1} \cdot q_b + c_{v2} \cdot q_{uf} + (1-c_{v0}) \cdot P_v$$

in which:

$$c_{a0} = \frac{R_f + R_v}{R_d + R_f + R_v} \quad c_{a1} = -\frac{R_d \cdot R_f}{R_d + R_f + R_v} \quad c_{a2} = -\frac{R_d \cdot R_v}{R_d + R_f + R_v}$$

$$c_{v0} = \frac{R_v}{R_d + R_f + R_v} \quad c_{v1} = \frac{R_f \cdot R_v}{R_d + R_f + R_v} \quad c_{v2} = -\frac{R_v \cdot (R_d + R_f)}{R_d + R_f + R_v}$$

The third operating mode (as the following fourth and fifth operating modes) calculates at least a part of the coefficients $c_{a0}, c_{a1}, c_{a2}$ and $c_{v0}, c_{v1}, c_{v2}$ and from these derives $R_d$, $R_f$ and $R_v$. The calculation of the coefficients is done starting from one or more known values for each of the following quantities: $P_a, q_b, q_{uf}, P_v, P_{af}$ and $P_{vf}$. The quantities $P_a, q_b, q_{uf}, P_v$ are known through measurement. The quantities $P_{af}$ and $P_{vf}$ are known by direct measurement of the pressures in the vascular access, or by a process of calculation starting from the measurement of the pressures in the machine $P_{am}$ and $P_{vm}$.

As the number of coefficients $c_{a0}, c_{a1}, c_{a2}, c_{v0}, c_{v1}, c_{v2}$ is greater than the number of the resistances $R_d$, $R_f$ and $R_v$, there exists a multiplicity of relations between the coefficients and the resistances. In general, knowledge of three coefficients enables a determination of the resistances.

In the third operating mode both flow rates $q_b$ and $q_{uf}$ are varied and the arterial pressure in the machine $P_{am}$ is measured, from which arterial pressure in the vascular access $P_{af}$ is calculated.

In a specific embodiment in a first stage the pressure $P_{am}$ at flow rates $q_b=0$ and $q_{uf}=0$ is measured; in a second stage pressure $P_{am}$ at flow rates $q_b \ne 0$ and $q_{uf}=0$ is measured; in a third stage pressure $P_{am}$ at flow rates $q_b \ne 0$ and $q_{uf} \ne 0$ is measured.

More in general, $q_b$ at $q_f$=constant (for example=0) is varied and $P_{am}$ is measured at different values of $q_b$. Thereafter $q_{uf}$ at $q_b$=constant (for example $\ne 0$) is varied and $P_{am}$ measured at different values of $q_{uf}$.

In this third operating mode a mathematical model of the vascular access is used which is represented by one equation only:

$$P_{af} = c_{a0} \cdot P_a + c_{a1} \cdot q_b + c_{a2} \cdot q_{uf} + (1-c_{a0}) \cdot P_v$$

from which coefficients $c_{a0}, c_{a1}, c_{a2}$ can be derived, which are sufficient by themselves for the calculation of the three resistances $R_d, R_f, R_v$.

In this third operating mode at least one measurement is taken of the patient's arterial pressure $P_a$. Further, distal venous pressure $P_v$ is assumed to be zero; for this reason the equation used is simplified as follows:

$$P_{af} = c_{a0} \cdot P_a + c_{a1} \cdot q_b + c_{a2} \cdot q_{uf}$$

The third operating mode is now described step by step.

a. Determine values $P_{af0}$ of the arterial pressure in the vascular access (fistula) and the systemic arterial pressure of the patient $P_{a0}$ at a known ultrafiltration flow rate $q_{uf1}=0$ at a predetermined blood pump flow rate $q_b=0$.

b. Save and store values $P_{a0}$ and $P_{af0}$.

c. Calculate $c_{a0}$ by means of the equation $$c_{a0} = \frac{P_{af0}}{P_{a0}}$$

d. Save and store value $c_{a0}$.

e. Change the blood flow rate $q_b$ to a known value $q_{b1}$. At the same time the ultrafiltration flow rate $q_f$ is kept constant and equal to the flow rate at point a. (=0).

f. Determine values $P_{af1}$ and $P_{a1}$ of the arterial pressure in the vascular access (fistula) and, respectively, of the patient at blood pump flow rate $q_{b1}$.

g. Save and store values $q_{b1}, P_{af1}$ and $P_{a1}$.

h. Steps d-f can be repeated for a desired number of times so as to save and store a series of values $q_{bi}, P_{afi}, P_{ai}$, with i=1, 2, 3, ..., N, where N is an integer number greater than or equal to 1.

i. Determine $c_{a1}$ by solving the system of equations:

$$P_{afi} - c_{a0} \cdot P_{ai} = c_{a1} \cdot q_{bi}$$

with i=1, ..., N (N≧1)

If N=1 it is sufficient to solve a linear equation with only an unknown quantity.

If N>1 the value of $c_{a1}$ is found by means of an optimisation algorithm which determines the optimal solution for the above-cited system. The searched-for value can be the value of $c_{a1}$ which minimises the error between the values of $P_{af}$ calculated with the above system of equations, $P_{afi}^*$, where the asterisk * indicates that the value has been calculated, and the $P_{afi}$ values determined by measuring a pressure correlated with $P_{af}$. The optimisation algorithm can be, for example, a linear regression algorithm.

j. Save and store value $c_{a1}$.

k. Change the ultrafiltration flow rate to a known value $q_{uf1}$ not zero. At the same time the blood flow rate $q_b$ has a known value $q_{bk}$ different to zero.

l. Determine values $P_{af1}$ and $P_{a1}$ of the arterial pressure in the vascular access (fistula) and, respectively, of the patient at ultrafiltration flow rate $q_{uf1}$.

m. Save and store values $q_{bk}, q_{uf1}, P_{af1}$ and $P_{a1}$.

n. Steps k-m can be repeated for a desired number of times in order to store a series of values $q_{ufj}, P_{afj}, P_{aj}$, with j=1, 2, ..., M, where M is an integer number equal to or greater than 1.

o. Determine $c_{a2}$ by solving the following system of equations $$P_{afj} - c_{a0} \cdot P_{aj} - c_{a1} \cdot q_{bk} = c_{a2} \cdot q_{ufj}$$

with j=1, 2, ..., M (M≧1)

If M=1 it is sufficient to solve a linear equation with only an unknown quantity.

If M>1 the value of $c_{a2}$ is found by means of an algorithm of optimisation which determines the optimal solution for the above system. The sought-after value can be the value of $c_{a2}$ which minimises the error between the values of $P_{af}$ calculated using the system of equations $P_{afj}^*$, where the asterisk * indicates that the value is a calculated one, and the values of $P_{afj}$ determined through measuring a pressure correlated by $P_{af}$. The optimisation algorithm can be, for example, a linear regression algorithm (as at point i. above).

p. Save and store the determined value of $c_{a2}$.

q. Determine $R_f, R_v$ and $R_d$ by solving the following system of equations which express the relation between $c_{a0}, c_{a1}, c_{a2}$ and $R_d, R_f, R_v$.

$$R_f = -c_{a1} \cdot \left(1 + \frac{1}{1/c_{a0} - 1}\right)$$

$$R_v = -c_{a2} \cdot \left(1 + \frac{1}{1/c_{a0} - 1}\right)$$

$$R_d = (1/c_{a0} - 1) \cdot (R_f + R_v)$$

The value of the resistance $R_f$ can already be determined at step j. as both $c_{a0}$ and $c_{a1}$ are already known.

r. Save and store the first determined values of $R_f, R_v$ and $R_d$.

s. Determine $q_a$ using one of the equations of the mathematical model of the vascular access, for example:

$$q_a = \frac{P_a - P_{af}}{R_d}$$

t. Save and store the value calculated for $q_a$.

In steps from l. to n. the operation of measuring $P_{aj}$ can be omitted; in this case the values stored and used for the calculation are the same $P_{ai}$ values calculated at point h. at $q_b=q_{b1}$ and $q_{uf}=0$, or at point a. at $q_b=0$ and $q_{uf}=0$.

Fourth Monitoring Procedure.

Varying $q_b$ at $q_{uf}$=constant (for example zero) and measuring $P_{am}$ and $P_{vm}$.

In this case too we calculate at least a part of the coefficients $c_{a0}$, $c_{a1}$, $c_{a2}$ and $c_{v0}$, $c_{v1}$, $c_{v2}$ from which $R_d$, $R_f$ and $R_v$ are obtained. The calculation of the coefficients is done starting from the knowledge of one or more values for each of the following quantities: $P_a$, $q_b$, $q_{uf}$, $P_v$, $P_{af}$ and $P_{vf}$. The quantities $P_a$, $q_b$, $q_{uf}$, $P_v$ are known by measurements. The quantities $P_{af}$ and $P_{vf}$ are known by direct measurement of the pressures in the vascular access, or by means of a calculation process which uses the measured values of pressures $P_{am}$ and $P_{vm}$ in the extracorporeal circuit.

In the fourth operating mode the measures were taken at $q_{uf}=0$ and we use a mathematical model which includes both equations of $P_{af}$ and $P_{vf}$ which in this case are simplified into the following formulation:

$$P_{af}=c_{a0} \cdot P_a + c_{a1} \cdot q_b + (1-c_{a0}) \cdot P_v$$

$$P_{vf}=c_{v0} \cdot P_a + c_{v1} \cdot q_b + (1-c_{v0}) \cdot P_v$$

In the fourth operating mode the processor determines the four coefficients $c_{a0}$, $c_{a1}$, $c_{v0}$, and $c_{v1}$ and from these it calculates the three resistances $R_d$, $R_v$, $R_f$.

In the fourth operating mode the pressures $P_{af}$ and $P_{vf}$ in the vascular access are determined, either by direct measuring or by measuring pressures $P_{am}$ e $P_{vm}$ in the extracorporeal circuit and calculating $P_{af}$ and $P_{vf}$ by means of a mathematical model. The pressures $P_{af}$ and $P_{vf}$ are determined at different values of the blood flow rate $q_b$. In the fourth operating mode, the arterial and venous pressures $P_a$ and $P_v$ of the patient are also considered in the calculation of the coefficients.

As coefficients $c_{a0}$, $c_{a1}$, $c_{v0}$, and $c_{v1}$ are greater in number than resistances $R_d$, $R_f$ and $R_v$, there exists a multiplicity of relations between the coefficients and resistances. In general the knowledge of three coefficients enables determination of the resistances. It has been found that the most precise determination of the resistances $R_d$, $R_f$ and $R_v$ is obtained by using the three coefficients, $c_{a0}$, $c_{a1}$, and $c_{v0}$.

The fourth operating mode is now described step by step.

a. Determine pressures $P_{af}$, $P_{vf}$, $P_a$, and $P_v$ with the blood pump flow rate and the ultrafiltration flow rate at nil ($q_b=0$ and $q_{uf}=0$).
b. The values thus determined, $P_{af0}$, $P_{vf0}$, $P_{a0}$ and $P_v$, are stored in memory.
c. The processor calculates $c_{a0}$ and $c_{v0}$ by means of the equations:

$$c_{a0} = \frac{P_{af0} - P_{v0}}{P_{a0} - P_{v0}}$$

$$c_{v0} = \frac{P_{vf0} - P_{v0}}{P_{a0} - P_{v0}}$$

d. Change the blood flow rate to a known value $q_b=q_{b1} \neq 0$.

e. Determine at least one value of $P_{af}$, $P_{vf}$, $P_a$ and $P_v$ when $q_b=q_{b1}$.
f. Save and store values $P_{af1}$, $P_{vf1}$, $P_{a1}$ and $P_{v1}$ above-determined.
g. Repeat steps from d. to f. for a predetermined number of times N in order to obtain a series of values $q_{bi}$, $P_{afi}$, $P_{vfi}$, $P_{ai}$ and $P_{vi}$ with $i=1, 2, \ldots, N$ ($N \geq 1$).
h. calculate $c_{a1}$ as a solution for the system of equations $$P_{afi} - c_{a0} \cdot P_{ai} - (1-c_{a0}) \cdot P_{vi} = c_{a1} \cdot q_{bi}$$

If N=1 the solution is immediate. If N>1 the solution is obtainable with an optimization algorithm, such as for example a linear regression algorithm.

i. Save and store the value of $c_{a1}$.
j. Determine resistances $R_d$, $R_f$ and $R_v$ by solving the following equations which express the relation between $c_{a0}$, $c_{a1}$, $c_{v0}$ and $R_d$, $R_f$, $R_v$:

$$R_d = \frac{c_{a1}}{c_{v0} - c_{a0}}$$

$$R_f = \frac{c_{a1}}{c_{a0} - 1}$$

$$R_v = \frac{c_{a1} \cdot c_{v0}}{(c_{a0} - c_{v0}) \cdot (c_{a0} - 1)}$$

k. Save and store values $R_d$, $R_f$, and $R_v$ above-determined.
l. Determine the flow rate of the vascular access $q_a$ using one of the equations of the mathematical model, for example the second:

$$P_{af} - P_{vf} = R_f (q_a - q_b)$$

At point e., determination of the value of $P_v$ can be performed in two ways.

The first consists in considering $P_v$ constant ($P_v = P_{v0}$) during variation in the blood flow rate $q_b$, thus ignoring the variations in the venous pressure $P_v$ which actually occur during the various operative stages. Consequently the system of equations of point h. can be rewritten in the following way:

$$P_{afi} - c_{a0} \cdot P_{ai} - (1-c_{a0}) \cdot P_{v0} = c_{a1} \cdot q_{bi}$$

The second way consists in considering the variations in $P_v$ to be proportional to the variations in the arterial pressure $P_a$, thus:

$$P_{vi} = P_{v0} \cdot \frac{P_{ai}}{P_{a0}}$$

This is equivalent to assuming resistances $R_d$, $R_f$ and $R_v$ to be constant during variation of $q_b$.

In this case the equation of point h. is:

$$P_{afi} - c_{a0} \cdot P_{ai} - (1-c_{a0}) \cdot P_{v0} \cdot \frac{P_{ai}}{P_{a0}} = c_{a1} \cdot q_{bi}$$

Note that by substituting, in the above equation, $c_{a0}$ with the expression $$c_{a0} = \frac{P_{af0} - P_{v0}}{P_{a0} - P_{v0}}$$

as in point c. of the present operating mode, the following equation is obtained:

$$P_{afi} - \frac{P_{af0}}{P_{a0}} \cdot P_{ai} = c_{a1} \cdot q_{bi}$$

which is the same equation that appears at point i. of the third operating mode, in which the contribution of $P_v$ was ignored.

Fifth Monitoring Procedure.

The fifth operating mode is similar to the third, with the difference that, instead of determining $P_{af}$, $P_{vf}$ is determined.

Briefly, the fifth operating mode consists in varying the blood flow rate $q_b$ while maintaining the ultrafiltration rate $q_{uf}$ constant, in varying the ultrafiltration rate while keeping the blood flow rate $q_b$ constant, and in determining the venous pressure in the vascular access $P_{vf}$ at various values of the above-mentioned flow rates. The processor determines the resistances $R_d$, $R_f$ and $R_v$ and the flow rate $q_a$ in the vascular access by calculating the coefficients $c_{v0}$, $c_{v1}$, $c_{v2}$ using the equation $$P_{vf} = c_{v0} \cdot P_a + c_{v1} \cdot q_b + c_{v2} \cdot q_{uf} + (1-c_{v0}) \cdot P_v$$

and the operative stages cited for the third operative mode.

The resistances are calculated by solving the following system of equations:

$$c_{v0} = \frac{R_v}{R_d + R_f + R_v}$$

$$c_{v1} = \frac{R_f \cdot R_v}{R_d + R_f + R_v}$$

$$c_{v2} = -\frac{R_v \cdot (R_d + R_f)}{R_d + R_f + R_v}$$

The flow rate of the vascular access $q_a$ is calculated as in the third operative mode.

Note that, by means of the second monitoring procedure, $q_a$ and $R_v$ can be derived by determining two or more values for the venous pressure alone ($P_{vm}$ in the machine or $P_{vf}$ in the fistula), with the equation $$P_{vf} - P_v = R_v \cdot (q_a - q_{uf})$$

while for the calculation of the values of $R_f$ and $R_d$, the values of arterial pressure ($P_{am}$ or $P_{af}$) are also used, as well as the other two equations of the mathematical model:

$$q_a = \frac{P_a - P_{af}}{R_d} \quad \text{and} \quad P_{af} - P_{vf} = R_f \cdot (q_a - q_b).$$

Similarly a further monitoring procedure can be formulated on the basis of which the values of $q_a$ and $R_d$ are calculated, determining two or more values of only the arterial pressure ($P_{am}$ in the machine or $P_{af}$ in the fistula), using the equation $$q_a = \frac{P_a - P_{af}}{R_d}$$

while for calculating the values of $R_f$ and $R_v$ the values of the venous pressure ($P_{vm}$ or $P_{vf}$) are also used, as well as the other two equations of the mathematical model:

$$P_{vf} - P_v = R_v \cdot (q_a - q_{uf})$$

and $$P_{af} - P_{vf} = R_f \cdot (q_a - q_b).$$

In all of the above-described modes, the measurements are taken with the system in a steady state. For example, the various measurements are taken after a certain time interval (for example about ten seconds) after the blood flow rate or the ultrafiltration rate has been changed.

Two numerical examples of the application of the invention are now reported.

First Example

This example uses the above-described first monitoring procedure, applied to the apparatus of FIG. 1.

Direct measurement of pressures $P_a$, $P_{af}$, $P_{vf}$ were taken at different flow rate values $q_b$. The measurements taken are reported in the following table.

| $q_b$ (ml/min) | $P_a$ (mmHg) | $P_{af}$ (mmHg) | $P_{vf}$ (mmHg) | $\Delta P_f$ (mmHg) |
|---|---|---|---|---|
| 300 | 100 | 51 | 42 | 9 |
| 200 |  | 52 | 41 | 11 |
| 100 |  | 54 | 40 | 14 |
| 400 |  | 51 | 42 | 9 |
| 500 |  | 50 | 43 | 7 |

Figure 4:
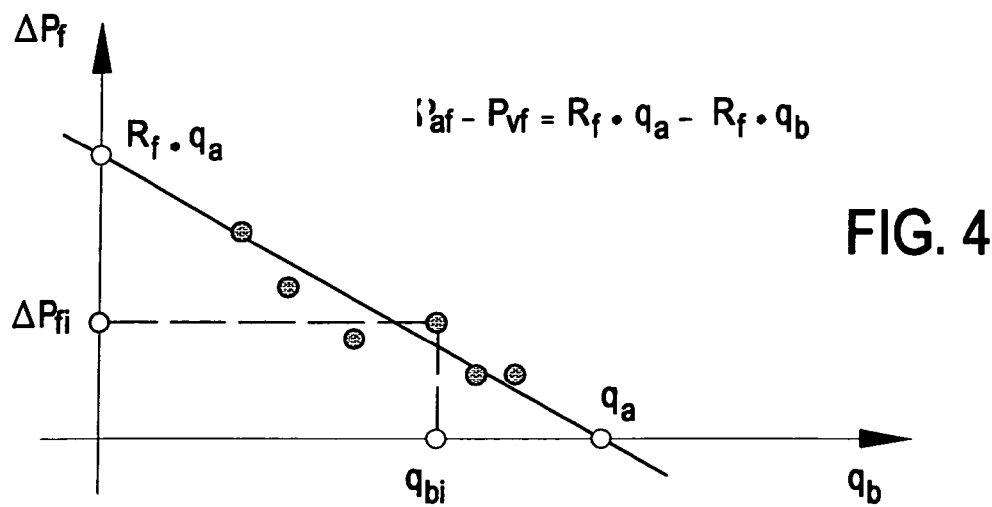
FIG. 4 shows a diagram of the relation between $\Delta P_f$ and $q_b$, where $\Delta P_f = P_{af} - P_{vf}$ (difference between arterial pressure in the vascular access $P_{af}$ and venous pressure in the vascular access $P_{vf}$) and $q_b$ is the extracorporeal flow rate of the blood.

The equation of the straight line interpolating points $\Delta P_f$ is as follows (see FIG. 4, where $\Delta P_f$ is a function of $q_b$):

$$\Delta P_f = 0.016 \cdot (925 - q_b)$$

From which the following values are calculated $R_f = 0.016$ mmHg·min/ml $q_a = 925$ ml/min From the third equation of the mathematical model used (assuming $P_v = 0$) we have $q_{b1} = 300$ ml/min:

$$R_v = \frac{P_{vf1}}{q_a} = 0.045 \text{ mmHg·min/ml}$$

Given $P_a = 100$ mmHg, for $q_{b1} = 300$ ml/min we obtain:

$$R_d = \frac{P_a - P_{af1}}{q_a} = 0.053 \text{ mmHg·min/ml}$$

Second Example

The second example uses the fourth monitoring procedure.

In the following the values of the pressure measured at different blood pump flow rates are reported.

| $q_b$ (ml/min) | $P_a$ (mmHg) | $P_{af}$ (mmHg) | $P_{vf}$ (mmHg) | $\Delta P_v$ (mmHg) |
|---|---|---|---|---|
| 0 | 120 | 62 | 35 | 0 |
| 150 | 118 | 59 | 37 | |
| 250 | 117 | 57 | 37 | |
| 350 | 114 | 53 | 38 | |

From these values we obtain:

$$c_{a0} = \frac{P_{af0} - P_{v0}}{P_{a0} - P_{v0}} = 0.52$$

$$c_{v0} = \frac{P_{vf0} - P_{v0}}{P_{a0} - P_{v0}} = 0.29$$

By applying a linear regression algorithm to the following equation:

$$P_{afi} - c_{a0} \cdot P_{ai} - (1-c_{a0}) \cdot P_{v0} = c_{a1} \cdot q_{bi}$$

the following value for coefficient $c_{a1}$ was found:

$$c_{a1} = -0.0155$$

After which the following resistance values were found:

$R_d = 0.069$ mmHg·min/ml $R_f = 0.032$ mmHg·min/ml $R_v = 0.042$ mmHg·min/ml

From this we calculated:

$$q_a = \frac{P_{af0} - P_{vf0}}{R_f} = 842 \text{ ml/min}$$

The invention claimed is:

1. A method of monitoring a vascular access associated with an extracorporeal blood circuit, comprising the stages of:
    storing in memory at least one mathematical model of the vascular access;
    varying the flow rate of at least one fluid in at least one of the extracorporeal blood circuit and at least one fluid transport line cooperating with the extracorporeal blood circuit;
    determining the values assumed by the pressure of the blood in at least one zone of the blood circulation path and with at least two different values of the flow rate of said at least one fluid;
    storing in memory the values of the pressure of the blood and the corresponding values of the flow rate of said at least one fluid; and
    processing the values stored in memory by means of the mathematical model, in order to determine at least one value of a characteristic of the vascular access;
    wherein the stage of determining the values assumed by the pressure of the blood comprises the following sub-stages:
        determining the values of the pressure of the blood in at least a first zone of the blood circulation path and for at least two different first values of the flow rate of said fluid; and
        determining the values of the pressure of the blood in at least a second zone of the blood circulation path and for at least two different second values of the flow rate of said fluid, said second zone being distant from said first zone.

2. The method of claim 1, wherein said at least two different first values are equal to said two different second values.

3. The method of claim 1, wherein said stage of varying the flow rate of at least one fluid comprises varying the flow rate of the blood in the extracorporeal circuit.

4. The method of claim 1, wherein said values assumed by the pressure of the blood are determined in at least two different zones of the blood circulation path.

5. The method of claim 1, comprising the stage of determining at regular intervals the values of the pressure of the blood in at least one zone of the blood circulation path during at least one flow rate variation, and
    wherein said stage of processing the values comprises evaluating the variation in said determined pressure values and using, in determining at least one value of a characteristic of the vascular access, the values of the pressure of the blood when said variation exceeds a threshold value.

6. The method of claim 5, wherein said threshold value is about 2 mmHg.

7. The method of claim 1, comprising the stages of:
    determining at regular intervals the values of the pressure of the blood in at least a first zone and a second zone of the blood circulation path during at least one flow rate variation;
    calculating the difference between the variation of the pressure of the blood detected in said first zone and the variation of the pressure of the blood detected in said second zone; and
    using, in determining at least one value of said characteristic of the vascular access, the values of the pressure of the blood when said difference has exceeded a threshold value.

8. The method of claim 7, wherein said threshold value is about 2 mmHg.

9. The method of claim 1, wherein the extracorporeal blood circuit comprises a blood withdrawal line connected to a blood withdrawal zone of the vascular access of a patient, and a blood return line connected to a blood return zone of the vascular access.

10. The method of claim 9, wherein the value of the pressure of the blood is determined by measurement thereof in a zone of the extracorporeal blood circuit located downstream of the blood withdrawal zone.

11. The method of claim 9, wherein a blood pump operates in the extracorporeal blood circuit to displace the blood, and
    wherein the value of the pressure of the blood is determined by measurement thereof in a zone of the extracorporeal blood circuit located upstream of the blood pump.

12. The method of claim 9, wherein the value of the pressure of the blood is determined by measurement thereof in the blood withdrawal zone.

13. The method of claim 9, wherein the value of the pressure of the blood is determined by measurement thereof in a zone of the extracorporeal blood circuit located upstream of the blood return zone.

14. The method of claim 9, wherein the value of the pressure of the blood is determined by measurement thereof in the blood return zone.

15. The method of claim 1, wherein a blood treatment unit is operatively associated to the extracorporeal blood circuit, and wherein the value of the pressure of the blood is determined by measurement performed downstream of the blood treatment unit.

16. A method of monitoring a vascular access associated with an extracorporeal blood circuit, comprising the stages of:
storing in memory at least one mathematical model of the vascular access;
varying the flow rate of at least one fluid in at least one of the extracorporeal blood circuit and at least one fluid transport line cooperating with the extracorporeal blood circuit;
determining the values assumed by the pressure of the blood in at least one zone of the blood circulation path and with at least two different values of the flow rate of said at least one fluid;
storing in memory the values of the pressure of the blood and the corresponding values of the flow rate of said at least one fluid; and
processing the values stored in memory by means of the mathematical model, in order to determine at least one value of a characteristic of the vascular access;
wherein the mathematical model of the vascular access comprises at least a first parameter relating to said characteristic of the vascular access, at least a second parameter relating to the pressure of the blood, and at least a third parameter relating to the flow rate of said at least one fluid;
wherein said characteristic of the vascular access is a characteristic selected from a group including: the blood flow rate $q_a$ upstream of a blood withdrawal zone from the vascular access; the blood flow rate $q_f$ between the blood withdrawal zone and a blood return zone at the vascular access; the blood flow rate $q_v$ downstream of the blood return zone; the vascular hydraulic resistance $R_d$ upstream of the blood withdrawal zone; the vascular hydraulic resistance $R_f$ between the blood withdrawal zone and the blood return zone; the vascular hydraulic resistance $R_v$ downstream of the blood return zone; and
wherein the mathematical model comprises one or more of the following equations:

$$q_a = \frac{P_a - P_{af}}{R_d}$$

$$P_{af} - P_{vf} = R_f \cdot (q_a - q_b)$$

$$P_{vf} - P_v = R_v \cdot (q_a - q_{vf}).$$

17. The method of claim 16, wherein said at least two different first values are equal to said two different second values.

18. The method of claim 16, wherein said values assumed by the pressure of the blood are determined in at least two different zones of the blood circulation path.

19. The method of claim 16, wherein a blood treatment unit is operatively associated to the extracorporeal blood circuit, and
wherein the value of the pressure of the blood is determined by measurement performed downstream of the blood treatment unit.

20. A method of monitoring a vascular access associated with an extracorporeal blood circuit, comprising the stages of:
storing in memory at least one mathematical model of the vascular access;
varying the flow rate of at least one fluid in at least one of the extracorporeal blood circuit and at least one fluid transport line cooperating with the extracorporeal blood circuit;
determining the values assumed by the pressure of the blood in at least one zone of the blood circulation path and with at least two different values of the flow rate of said at least one fluid;
storing in memory the values of the pressure of the blood and the corresponding values of the flow rate of said at least one fluid; and
processing the values stored in memory by means of the mathematical model, in order to determine at least one value of a characteristic of the vascular access;
wherein said stage of varying the flow rate of at least one fluid comprises varying the flow rate of a first fluid flowing in the extracorporeal circuit, and varying the flow rate of a second fluid flowing in a fluid transport line connected to the extracorporeal circuit, and
wherein said stage of determining the values assumed by the pressure of the blood comprises determining said values in at least one zone of the blood circulation path, with at least two different values of the flow rate of the first fluid, and with at least two different values of the flow rate of the second fluid.

21. The method of claim 20, wherein said at least two different first values are equal to said two different second values.

22. The method of claim 20, wherein said values assumed by the pressure of the blood are determined in at least two different zones of the blood circulation path.

23. The method of claim 20, wherein a blood treatment unit is operatively associated to the extracorporeal blood circuit, and
wherein the value of the pressure of the blood is determined by measurement performed downstream of the blood treatment unit.

24. A method of monitoring a vascular access associated with an extracorporeal blood circuit, comprising the stages of:
storing in memory at least one mathematical model of the vascular access;
varying the flow rate of at least one fluid in at least one of the extracorporeal blood circuit and at least one fluid transport line cooperating with the extracorporeal blood circuit;
determining the values assumed by the pressure of the blood in at least one zone of the blood circulation path and with at least two different values of the flow rate of said at least one fluid;
storing in memory the values of the pressure of the blood and the corresponding values of the flow rate of said at least one fluid; and
processing the values stored in memory by means of the mathematical model, in order to determine at least one value of a characteristic of the vascular access;
wherein said stage of varying the flow rate of at least one fluid comprises varying a flow rate of a discharge fluid in a drainage line connected to the extracorporeal circuit through a semi-permeable membrane of an extracorporeal blood treatment unit.

25. The method of claim 24, wherein said at least two different first values are equal to said two different second values.

26. The method of claim 24, wherein said values assumed by the pressure of the blood are determined in at least two different zones of the blood circulation path.

27. The method of claim 24, wherein a blood treatment unit is operatively associated to the extracorporeal blood circuit, and wherein the value of the pressure of the blood is determined by measurement performed downstream of the blood treatment unit.

28. A method of monitoring a vascular access associated with an extracorporeal blood circuit, comprising the stages of:

storing in memory at least one mathematical model of the vascular access;

varying the flow rate of at least one fluid in at least one of the extracorporeal blood circuit and at least one fluid transport line cooperating with the extracorporeal blood circuit;

determining the values assumed by the pressure of the blood in at least one zone of the blood circulation path and with at least two different values of the flow rate of said at least one fluid;

storing in memory the values of the pressure of the blood and the corresponding values of the flow rate of said at least one fluid; and processing the values stored in memory by means of the mathematical model, in order to determine at least one value of a characteristic of the vascular access;

wherein said stage of varying the flow rate of at least one fluid comprises varying the flow rate of the blood in the extracorporeal blood circuit, and varying the flow rate of a discharge fluid in a drainage line connected to the extracorporeal blood circuit through a semi-permeable membrane of an extracorporeal blood treatment unit.

29. The method of claim 28, wherein said at least two different first values are equal to said two different second values.

30. The method of claim 28, wherein said values assumed by the pressure of the blood are determined in at least two different zones of the blood circulation path.

31. The method of claim 28, wherein a blood treatment unit is operatively associated to the extracorporeal blood circuit, and wherein the value of the pressure of the blood is determined by measurement performed downstream of the blood treatment unit.

32. A method of monitoring a vascular access associated with an extracorporeal blood circuit, comprising the stages of:

storing in memory at least one mathematical model of the vascular access;

varying the flow rate of at least one fluid in at least one of the extracorporeal blood circuit and at least one fluid transport line cooperating with the extracorporeal blood circuit;

determining the values assumed by the pressure of the blood in at least one zone of the blood circulation path and with at least two different values of the flow rate of said at least one fluid;

storing in memory the values of the pressure of the blood and the corresponding values of the flow rate of said at least one fluid; and processing the values stored in memory by means of the mathematical model, in order to determine at least one value of a characteristic of the vascular access;

wherein the mathematical model comprises at least one parameter relating to a characteristic of the systemic circulation of a patient connected to the extracorporeal blood circuit.

33. The method of claim 32, wherein at least one value for said characteristic of the systemic circulation of a patient is determined and stored in memory, said stored value being processed by means of the mathematical model in order to determine said at least one value of a characteristic of the vascular access.

34. The method of claim 32, wherein said characteristic of the systemic circulation of the patient is the systemic arterial pressure.

35. The method of claim 32, wherein said at least two different first values are equal to said two different second values.

36. The method of claim 32, wherein said values assumed by the pressure of the blood are determined in at least two different zones of the blood circulation path.

37. The method of claim 32, wherein a blood treatment unit is operatively associated to the extracorporeal blood circuit, and wherein the value of the pressure of the blood is determined by measurement performed downstream of the blood treatment unit.

38. A method of monitoring a vascular access associated with an extracorporeal blood circuit, comprising the stages of:

storing in memory at least one mathematical model of the vascular access;

varying the flow rate of at least one fluid in at least one of the extracorporeal blood circuit and at least one fluid transport line cooperating with the extracorporeal blood circuit;

determining the values assumed by the pressure of the blood in at least one zone of the blood circulation path and with at least two different values of the flow rate of said at least one fluid;

storing in memory the values of the pressure of the blood and the corresponding values of the flow rate of said at least one fluid; and processing the values stored in memory by means of the mathematical model, in order to determine at least one value of a characteristic of the vascular access;

wherein said values of the pressure of the blood are determined during a steady state, said steady state being reached after having maintained the flow rate of said at least one fluid constant for a determined period of time.

39. The method of claim 38, wherein said at least two different first values are equal to said two different second values.

40. The method of claim 38, wherein said values assumed by the pressure of the blood are determined in at least two different zones of the blood circulation path.

41. The method of claim 38, wherein a blood treatment unit is operatively associated to the extracorporeal blood circuit, and wherein the value of the pressure of the blood is determined by measurement performed downstream of the blood treatment unit.

42. A method of monitoring a vascular access associated with an extracorporeal blood circuit, comprising the stages of:

storing in memory at least one mathematical model of the vascular access;

varying the flow rate of at least one fluid in at least one of the extracorporeal blood circuit and at least one fluid transport line cooperating with the extracorporeal blood circuit;

determining the values assumed by the pressure of the blood in at least one zone of the blood circulation path and with at least two different values of the flow rate of said at least one fluid;

storing in memory the values of the pressure of the blood and the corresponding values of the flow rate of said at least one fluid;

processing the values stored in memory by means of the mathematical model, in order to determine at least one value of a characteristic of the vascular access; and determining at regular intervals the values of the pressure of the blood in at least one zone of the blood circulation path during at least one flow rate variation;

wherein said stage of processing the values comprises evaluating the variation in said determined pressure values and using, in determining at least one value of a characteristic of the vascular access, the values of the pressure of the blood when said variation exceeds a threshold value, and wherein said threshold value is about 2 mmHg.

* * * * *